(12) United States Patent  
Lu et al.

(10) Patent No.: US 11,110,199 B2  
(45) Date of Patent: Sep. 7, 2021

(54) METHODS FOR HOST CELL HOMING AND DENTAL PULP REGENERATION

(71) Applicant: The Trustees of Columbia University in the City of New York, New York, NY (US)

(72) Inventors: Helen H. Lu, New York, NY (US); Sagaw Prateepchinda, Nonthaburi (TH); Gunnar Hasselgren, Tenafly, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 114 days.

(21) Appl. No.: 16/353,834

(22) Filed: Mar. 14, 2019

(65) Prior Publication Data

US 2019/0209734 A1    Jul. 11, 2019

Related U.S. Application Data

(63) Continuation of application No. 14/783,778, filed as application No. PCT/US2014/033866 on Apr. 11, 2014, now abandoned.

(Continued)

(51) Int. Cl.
*A61L 27/22* (2006.01)
*A61L 27/38* (2006.01)
(Continued)

(52) U.S. Cl.
CPC .......... *A61L 27/225* (2013.01); *A61K 9/0024* (2013.01); *A61K 9/06* (2013.01); *A61K 35/28* (2013.01); *A61K 35/32* (2013.01); *A61L 27/16* (2013.01); *A61L 27/18* (2013.01); *A61L 27/26* (2013.01); *A61L 27/3808* (2013.01); *A61L 27/3834* (2013.01); *A61L 27/3865* (2013.01); *A61L 27/48* (2013.01); *A61L 27/52* (2013.01); *A61L 27/54* (2013.01); *A61L 27/58* (2013.01);
(Continued)

(58) Field of Classification Search
None
See application file for complete search history.

(56) References Cited

U.S. PATENT DOCUMENTS

| 4,479,271 A | 10/1984 | Bolesky et al. |
| 5,024,669 A | 6/1991 | Peterson et al. |

(Continued)

FOREIGN PATENT DOCUMENTS

| JP | 6-154305 | 6/1994 |
| JP | 6-165817 | 6/1994 |

(Continued)

OTHER PUBLICATIONS

Communication Pursuant to Article 94(3) EPC dated Sep. 27, 2019 in connection with counterpart European Patent Application No. 14782570.7.

(Continued)

*Primary Examiner* — David W Berke-Schlessel  
(74) *Attorney, Agent, or Firm* — John P. White

(57) ABSTRACT

Hydrogel-based scaffolds useful for promoting pulp cell growth and biosynthesis, regulating pulp cell migration and morphology, or both as well as methods for their production and use are provided.

10 Claims, 11 Drawing Sheets

INFECTION → INFECTED PULP REMOVED VIA PULPOTOMY → HYDROGEL + ANTIBIOTIC RELEASE → PULP REGENERATION → PULP REPAIR

Related U.S. Application Data

(60) Provisional application No. 61/811,433, filed on Apr. 12, 2013.

(51) Int. Cl.

| | | |
|---|---|---|
| *A61K 35/32* | (2015.01) | |
| *A61L 27/26* | (2006.01) | |
| *A61L 27/52* | (2006.01) | |
| *A61K 35/28* | (2015.01) | |
| *A61L 27/48* | (2006.01) | |
| *A61L 27/58* | (2006.01) | |
| *C12N 5/0775* | (2010.01) | |
| *A61L 27/16* | (2006.01) | |
| *A61L 27/18* | (2006.01) | |
| *A61K 9/06* | (2006.01) | |
| *A61K 9/00* | (2006.01) | |
| *A61L 27/54* | (2006.01) | |

(52) U.S. Cl.
CPC ...... *C12N 5/0664* (2013.01); *A61L 2300/406* (2013.01); *A61L 2300/64* (2013.01); *A61L 2400/06* (2013.01); *A61L 2400/12* (2013.01); *A61L 2430/12* (2013.01); *C12N 2533/50* (2013.01)

(56) References Cited

U.S. PATENT DOCUMENTS

| | | |
|---|---|---|
| 5,078,745 A | 1/1992 | Rhenter et al. |
| 5,084,350 A | 1/1992 | Chang et al. |
| 5,108,436 A | 4/1992 | Chu et al. |
| 5,133,755 A | 7/1992 | Brekke |
| 5,308,701 A | 5/1994 | Cohen et al. |
| 5,366,508 A | 11/1994 | Brekke |
| 5,455,041 A | 10/1995 | Genco et al. |
| 5,549,676 A | 8/1996 | Johnson |
| 5,607,474 A | 3/1997 | Athanasiou et al. |
| 5,626,861 A | 5/1997 | Laurencin et al. |
| 5,683,459 A | 11/1997 | Brekke |
| 5,716,413 A | 2/1998 | Walter et al. |
| 5,755,792 A | 5/1998 | Brekke |
| 5,766,618 A | 6/1998 | Laurencin et al. |
| 5,849,331 A | 12/1998 | Ducheyne et al. |
| 5,855,610 A | 1/1999 | Vacanti et al. |
| 5,866,155 A | 2/1999 | Laurencin et al. |
| 5,885,829 A | 3/1999 | Mooney et al. |
| 5,904,717 A | 5/1999 | Brekke et al. |
| 5,922,025 A | 7/1999 | Hubbard |
| 5,944,754 A | 8/1999 | Vacanti |
| 6,005,161 A | 12/1999 | Brekke et al. |
| 6,013,591 A | 1/2000 | Ying et al. |
| 6,143,293 A | 11/2000 | Weiss et al. |
| 6,179,878 B1 | 1/2001 | Duerig et al. |
| 6,187,329 B1 | 2/2001 | Agrawal et al. |
| 6,187,742 B1 | 2/2001 | Wozney et al. |
| 6,235,061 B1 | 5/2001 | Laurencin et al. |
| 6,291,597 B1 | 9/2001 | Lyles et al. |
| 6,306,424 B1 | 10/2001 | Vyakarnam et al. |
| 6,328,765 B1 | 12/2001 | Hardwick et al. |
| 6,333,029 B1 | 12/2001 | Vyakarnam et al. |
| 6,365,149 B2 | 4/2002 | Vyakarnam et al. |
| 6,378,527 B1 | 4/2002 | Hungerford et al. |
| 6,409,764 B1 | 6/2002 | White et al. |
| 6,432,437 B1 | 8/2002 | Hubbard |
| 6,454,811 B1 | 9/2002 | Sherwood et al. |
| 6,459,948 B1 | 10/2002 | Ateshian et al. |
| 6,534,084 B1 | 3/2003 | Vyakarnam et al. |
| 6,541,022 B1 | 4/2003 | Murphy et al. |
| 6,544,503 B1 | 4/2003 | Vanderhoff et al. |
| 6,558,612 B1 | 5/2003 | Hubbard |
| 6,579,533 B1 | 6/2003 | Tormala et al. |
| 6,602,294 B1 | 8/2003 | Sittinger et al. |
| 6,626,950 B2 | 9/2003 | Brown et al. |
| 6,730,252 B1 | 5/2004 | Teoh et al. |
| 6,737,053 B1 | 5/2004 | Goh et al. |
| 6,787,518 B1 | 9/2004 | Kato et al. |
| 6,811,776 B2 | 11/2004 | Kale et al. |
| 6,852,330 B2 | 2/2005 | Bowman et al. |
| 6,984,623 B2 | 1/2006 | Celeste et al. |
| 6,995,013 B2 | 2/2006 | Connelly et al. |
| 7,087,200 B2 | 8/2006 | Taboas et al. |
| 7,105,182 B2 | 9/2006 | Szymaitis et al. |
| 7,112,417 B2 | 9/2006 | Vyakarnam et al. |
| 7,172,765 B2 | 2/2007 | Chu et al. |
| 7,217,294 B2 | 5/2007 | Kusanagi et al. |
| 7,252,685 B2 | 8/2007 | Bindseil et al. |
| 7,309,232 B2 | 12/2007 | Rutherford et al. |
| 7,319,035 B2 | 1/2008 | Vacanti et al. |
| 7,322,825 B2 | 1/2008 | Szymaitis |
| 7,326,426 B2 | 2/2008 | Nathan et al. |
| 7,351,250 B2 | 4/2008 | Zamierowski |
| 7,390,526 B2 | 6/2008 | Stupp et al. |
| 7,419,681 B2 | 9/2008 | Tormala et al. |
| 7,524,335 B2 | 4/2009 | Slivka et al. |
| 7,531,503 B2 | 5/2009 | Atala et al. |
| 7,674,289 B2 | 3/2010 | Xu |
| 7,704,740 B2 | 4/2010 | Schindler et al. |
| 7,767,221 B2 | 8/2010 | Lu et al. |
| 7,786,086 B2 | 8/2010 | Reches et al. |
| 7,803,574 B2 | 9/2010 | Desai et al. |
| 7,824,447 B2 | 11/2010 | Xu |
| 7,824,701 B2 | 11/2010 | Binette et al. |
| 7,842,737 B2 | 11/2010 | Wang et al. |
| 7,901,461 B2 | 3/2011 | Harmon et al. |
| 8,142,501 B2 | 3/2012 | Macossay-Torres |
| 8,168,431 B2 | 5/2012 | Brady et al. |
| 8,187,326 B2 | 5/2012 | Hammer et al. |
| 8,226,715 B2 | 7/2012 | Hwang et al. |
| 10,265,155 B2 * | 4/2019 | Lu ............................ B29C 67/04 |
| 2001/0000195 A1 | 4/2001 | Smith et al. |
| 2002/0095213 A1 | 7/2002 | Bakker et al. |
| 2002/0119177 A1 | 8/2002 | Bowman et al. |
| 2002/0127265 A1 | 9/2002 | Bowman et al. |
| 2002/0182241 A1 | 12/2002 | Borenstein et al. |
| 2002/0187104 A1 | 12/2002 | Li et al. |
| 2003/0004578 A1 | 1/2003 | Brown et al. |
| 2003/0026860 A1 | 2/2003 | Lasekan et al. |
| 2003/0071380 A1 | 4/2003 | Wang et al. |
| 2003/0114936 A1 | 6/2003 | Sherwood et al. |
| 2003/0147935 A1 | 8/2003 | Binette et al. |
| 2003/0175257 A1 | 9/2003 | Song et al. |
| 2003/0199615 A1 | 10/2003 | Chaput et al. |
| 2003/0225459 A1 | 12/2003 | Hammer et al. |
| 2004/0010320 A1 | 1/2004 | Huckle et al. |
| 2004/0033214 A1 | 2/2004 | Young et al. |
| 2004/0078090 A1 | 4/2004 | Binette et al. |
| 2004/0109845 A1 | 6/2004 | Terkeltaub |
| 2004/0122209 A1 | 6/2004 | Poole |
| 2004/0243235 A1 | 12/2004 | Goh et al. |
| 2005/0008675 A1 | 1/2005 | Bhatia et al. |
| 2005/0095695 A1 | 5/2005 | Shindler et al. |
| 2005/0118236 A1 | 6/2005 | Qiu et al. |
| 2005/0196425 A1 | 9/2005 | Zamora et al. |
| 2005/0205498 A1 | 9/2005 | Sowemimo-Coker et al. |
| 2005/0255583 A1 | 11/2005 | Depaola et al. |
| 2006/0165663 A1 | 7/2006 | Tanaka et al. |
| 2006/0204738 A1 | 9/2006 | Disbrow et al. |
| 2006/0273279 A1 | 12/2006 | Kaplan et al. |
| 2007/0071728 A1 | 3/2007 | Ko et al. |
| 2007/0231275 A1 | 10/2007 | Ueda |
| 2007/0244484 A1 | 10/2007 | Luginbuehl |
| 2007/0269481 A1 | 11/2007 | Li et al. |
| 2008/0026419 A1 | 1/2008 | Bottlang et al. |
| 2008/0044900 A1 | 2/2008 | Mooney et al. |
| 2008/0085292 A1 | 4/2008 | Rezania et al. |
| 2008/0170982 A1 | 7/2008 | Zhang et al. |
| 2008/0273206 A1 | 11/2008 | Genge et al. |
| 2008/0274185 A1 | 11/2008 | Mao |
| 2008/0274545 A1 | 11/2008 | Kuo et al. |
| 2009/0140406 A1 | 6/2009 | Lu et al. |
| 2009/0148486 A1 | 6/2009 | Lu et al. |
| 2009/0162643 A1 | 6/2009 | Dubrow et al. |

(56) References Cited

U.S. PATENT DOCUMENTS

| | | | |
|---|---|---|---|
| 2009/0196901 | A1 | 8/2009 | Guilak et al. |
| 2009/0317446 | A1 | 12/2009 | Tan et al. |
| 2010/0114547 | A1 | 5/2010 | Boyden et al. |
| 2010/0143439 | A1 | 6/2010 | Jayasuriya et al. |
| 2010/0168771 | A1 | 7/2010 | Guldberg et al. |
| 2010/0172952 | A1 | 7/2010 | Srouji et al. |
| 2010/0179659 | A1 | 7/2010 | Li et al. |
| 2010/0203481 | A1 | 8/2010 | Murray et al. |
| 2010/0234955 | A1 | 9/2010 | Santerre et al. |
| 2010/0303881 | A1 | 12/2010 | Hoke et al. |
| 2010/0331979 | A1 | 12/2010 | McDade et al. |
| 2011/0009963 | A1 | 1/2011 | Binnette et al. |
| 2011/0020917 | A1 | 1/2011 | Wen et al. |
| 2011/0038921 | A1 | 2/2011 | Wen et al. |
| 2011/0046734 | A1 | 2/2011 | Tobis et al. |
| 2011/0097406 | A1 | 4/2011 | Bryant et al. |
| 2011/0171607 | A1 | 7/2011 | Mao et al. |
| 2011/0201984 | A1 | 8/2011 | Dubrow et al. |
| 2011/0293685 | A1 | 12/2011 | Kuo et al. |
| 2012/0020911 | A1 | 1/2012 | Seliktar et al. |
| 2012/0029653 | A1 | 2/2012 | Evans et al. |
| 2012/0046758 | A1 | 2/2012 | Evans et al. |
| 2016/0296664 | A1 | 10/2016 | Lu et al. |

FOREIGN PATENT DOCUMENTS

| | | | |
|---|---|---|---|
| WO | WO 1998/022041 | A1 | 5/1998 |
| WO | WO 1999/007777 | A1 | 2/1999 |
| WO | WO 1999/033415 | A1 | 7/1999 |
| WO | WO 1999/055252 | A1 | 11/1999 |
| WO | WO 2001/034060 | A1 | 5/2001 |
| WO | WO 2005/042048 | | 5/2005 |
| WO | WO 2006/116530 | | 11/2006 |
| WO | WO 2008/091391 | A1 | 7/2008 |
| WO | WO 2008/128304 | A1 | 10/2008 |
| WO | WO 2009/055609 | | 4/2009 |
| WO | WO 2009/102967 | A2 | 8/2009 |
| WO | WO 2010/064251 | A1 | 6/2010 |
| WO | WO 2010/144992 | A1 | 12/2010 |
| WO | WO 2012/021885 | A1 | 2/2012 |
| WO | WO 2014/169249 | | 10/2014 |

OTHER PUBLICATIONS

About, I. et al., "Human dentin production in vitro," Exp. Cell Res. 258: 33-41, (2000).
About, I., "Influence of resinous monomers on the differentiation in vitro of human pulp cells into Odontoblasts," J. Biomed. Mater. Res. (Appl. Biomater.) 63:418-423,(2002).
Ada. Survey of Dental Practice. 5S99. 1999. American Dental Association.
Albandar, Jasim M., "Epidemiology and Risk Factors of Periodontal Diseases," Dent. Clin. N. Am. 49(3):511-532 (2005).
Alhadlaq, A. and Mao, J.J., "Tissue-Engineered Neogenesis of Human-Shaped Mandibular Condyle from Rat Mesenchyma Stem Cells," J. Dent. Res. 82(12):951-956 (2003).
Almany, L. and Seliktar, D., "Biosynthetic Hydrogel Scaffolds Made from Fibrinogen and Polyethylene Glycol for 3D Cell Cultures," Biomaterials. 26(15):2467-2477 (2005).
Almany, L. et al., "Biosynthetic hydrogel scaffolds made from fibrinogen and polyethylene gylcol for 3D cell cultures," Biomaterials. 26:2467-2477 (2005).
Almushayt, A., "The in-vio role of DMP2 in the Cytodifferentiation of undifferentiated mesenchymal pulp cells into odontoblast-like cells," Presented at IADR. J. Dent. Research. 81 (Spec. Iss. A)A-278 (2002).
Anderson, H. Clarke., "Electron Microscopic Studies of Induced Cartilage Development and Calcification," J. Cell Biol. 35(1):81-101 (1967).
Anderson, H. Clarke., "Molecular Biology of Matrix Vesicles," Clin. Orthap. Relat. Res. 314:266-280 (1996).
Anderson, H. Clarke., "Vesicles Associated with Calcification in the Matrix of Epiphyseal Cartilage," J. Cell Biol. 41(1):59-72 (1969).
Andreasen, J.O., "Replantation of 400 avulsed permanent Incirsors. 2. Factors related to pulp healing," Endod. Dent. Traumatol. 11:59-68 (1995).
Andreasen, J.O., "Replantation of 400-avulsed permanent Incisors. 1. Diagnosis of healing complications," Endod. Dent. Traumatol. 11:51-58 (1995).
Andreasen, J.O., "Replantation of 400 avulsed permanent incisors. 3. Factors related to root growth," Endod. Dent. Traumatol. 11:69-75 (1995).
Anitua, E., "Autologous preparations rich in growth factors promote proliferation and induce VEGF and HGF production by human tendon cells in culture," J. Orthop. Res. 23(2):281-286 (2005).
Baker et al., "The Relationship between the Mechanical Properties and Cell Behavior on PLGA and PCL Scaffolds for Bladder Tissue Engineering," Biomaterials. 30:1321-1328 (2009).
Banes, A.J., "Mechanoreception at the cellular level: the detection, interpretation, and diversity of responses to mechanical signals," Biochem. Cell Bio. 73:349-365 (1995).
Barkhordar R.A., et al., "lnterleukin-1 B activity and collagen synthesis in human dental pulp fibroblasts," J. Endod. 28:157-159 (2002).
Barthel et al., "Pulp Capping of Carious Exposures: Treatment Outcome after 5 and 10 Years: A Retrospective Study," J. Endod. 26:525-528 (2000).
Bartold, P.M. and Narayanan, A.S., "Molecular and Cell Biology of Healthy and Diseased Periodontal Tissues," Periodontol. 40:29-49 (2006).
Baumgartner, J.C., Pulpal infections including caries, in Seltzer and Bender's: Dental Pulp, Hargreaves, K.M., Goodis, H.E., Eds.; Quintessence Publishing Co, Inc.: Chicago, pp. 281-307 (2002).
Benjamin, M. and Ralphs, J.R., "Etheses—The Bony Attachments of Tendons and Ligaments," Ital. J. Anat. Embryol. 106(2 Suppl 1):151-157 (2000)(Abstract only).
Bernard, G.W. and Pease, D.C., An Electron Microscopic Study of Initial Intramembranous Osteogenesis, Am. J. Anat. 125:271-290 (1969).
Berrey et al., "Fractures of Allografts: Frequency, Treatment and End-Results," J. Bone Joint. Surg. Am. 72(6):825-833.
Bimstein, E. et al., "Enhanced healing of tooth-pulp wounds in the dog by enriched collagen solution as a capping agent," Arch. Oral Biol. 26:97-101 (1981).
Blandford et al., "Modeling of Matrix Vesicle Biomineralization Using Large Unilamellar Vesicle," J. Inorg. Biochem. 94(1-2):14-27.
Bohl et al., "Role of synthetic extracellular matrix in development of engineered dental pulp," J. Biomater. Sci. Polym. Ed. 9:749-764 (1998).
Boskey; A.L., Boyan, B.D. and Schwartz, Z., "Matrix Vesicles Promote Mineralization in Gelatin Gel," Calcif. Tissue Int. 60:309-315 (1997).
Boskey, A.L., et al., "Persistence of Complexed Acidic Phospholipids in Rapidly Mineralizing Tissues is Due to Affinity for Mineral and Resistance to Hydrolytic Attack: In Vitro Data," Calcif. Tissue Int. 58:45-51 (1996).
Bouhadir et al., "Promoting Angiogenesis in Engineered Tissues," Drug Target. 9:397-406 (2001).
Bouvier, et al., "In vitro mineralization of a three-dimensional collagen matrix by human dental pulp cells in the presence of chondroitin sulphate," Arch. Oral Biol. 35:301-309 (1990).
Brennan, M.T., et al., "The Impact of Oral Disease and Nonsurgical Treatment on Bactermia in Children," J. Am. Dent. Assoc. 138(1):80-85 (2007).
Briggs, P.F.A. et al., "Evidence-based dentistry: endodontic failure—how should it be managed?," Br. Dent. J. 183:159-164 (1997).
Brock, D.P. et al., "Alpha-smooth-muscle actin in and contraction of porcine dental pulp cells," J. Dent. Res. 81:203-208 (2002).
Brogi, E., et al., "Distinct Patterns of Expression of Fibroblast Growth Factors and their Receptors in Human Atheroma and Nonatherosclerotic Arteries. Association of Acidic FGF with Plaque Microvessels and Macrophages," J. Clin. Invest. 92(5):2408-2418 (1993).

(56) References Cited

OTHER PUBLICATIONS

Brooks, Peter M., "Impact of Osteoarthritis on Individuals and Society: How much Disability? Social Consequences and Health Economic Implications," Curr. Opin. Rheumatol, 14(5): 573-577 (2002).
Bruneau, Michael, et al., "Anterior Cervical Interbody Fusion with Hydroxyapatite Graft and Plate System," Neurosurg. Focus. 10(4):1-6 (2001).
Buehler, Markus J., "Molecular Nanomechanics of Nascent Bone: Fibrillar Toughening by Mineralization," Nanotechnology. 18:(295102-295111) (2007).
Buurma, B., et al., -"Transplantation of human pulpal and gingival fibroblasts attached to synthetic scaffolds," Eur. J. Oral Sci. 107:282-289 (1999).
Camolezi, Fernando, L., et al., "Construction of an Alkaline Phosphatase-Liposome System: A Tool for Biomineralization Study," Int. J. Biochem. Cell Biol. 34(9):1091-1101 (2002).
Chesnutt, Betsy M., et al., "Composite Chitosan/Nano-Hydroxyapatite Scaffolds Induce Osteocalcin Production by Osteoblasts In Vitro and Support Bone Formation In Vivo," Tissue Eng. Part A. 15(9):2571-2579 (2009).
Cheung, G.S.: "Endodontic failures-changing the approach," Inter. Dent. J. 46:131-138 (1996).
Chew, Sing Yian, et al., "Sustained Release of Proteins From Electrospun Biodegradable Fibers," Biomacromolecules. 6(4):2017-2024 (2005).
Cho, B.C. et al., "The bone regenerative effect of chitosan microsphere-encapsulated growth hormone on bony consolidation in mandibular distraction osteogenesis in a dog model," J. Craniofac. Surg. 15(2):299-311 (2004).
Choi, S.H. et al., "Effect of recombinant human bone morphogenetic protein-2/absorbable collagen sponge (rhBMP-2/ACS) on healing in 3-wall intrabony defects in dogs," J. Periodontol. 73(1):63-72 (2002).
Christensen, L.R., et al., "Immunocytochemical Demonstration of Nerve Growth Factor Receptor (NGF-R) in Developing Human Fetal Teeth," Anat. Embryol. 188(3):247-255 (1993).
Clark, P.A. et al., "Porous implants as drug delivery vehicles to augment host tissue integration," FASEB J. 22(6):1684-93 (2008).
Constantino, P.D., and Friedman, C.D., "Synthetic Bone Graft Substitutes," Otolaryngol Clin. North Am. 27(5):1037-1074 (1994).
Cook, Jeremy J., and Cook, Emily A., "Bioscaffolds and the Reconstruction of Ligaments and Tendons in the Foot and Ankle," Clin. Podiatr. Med. Surg. 26(4):535-543 (2009).
Costa, K.D., Lee, E.J., and Holmes, J.W., "Creating Alignment and Anistrophy in Engineered Heart Tissue: Role of Boundary Conditions in a Model Three-Dimensional Culture System," Tissue Eng. 9(4):567-577 (2003).
Couble, M.L., Farges, J.C., Bleicher, F., Perrat-Mabillon, B., Boudeulle, M., Magloire, H.; "Odontoblast differentiation of human dental pulp cells in explant cultures," Calcif. Tissue Int. 66:129-138 (2000).
Cox, C.F. et al., "Tunnel defects in dentin bridges: their formation following direct pulp capping," Oper. Dent. 21:(1)4-11 (1996).
Cvek, M., "A clinical report on partial pulpotomy and capping with calcium hydroxide in permanent incisors with complicated crown fracture," J. Endod. 4:232-237 (1978).
Cvek, M., et al., "Pulp revascularization in reimplanted immature monkey incisors predicatability and the effect on antibiotic systemic prophylaxis," Endod. Dent. Traumatol. 6:157-169 (1990).
Cvek, M., et al., "Effect of topical application of Doxycycline on pulp revascularization and periodontal Healing in reimplanted monkey incisors," Endod. Dent. Traumatol. 6:170-176 (1990).
Dahlen, G., Haapasalo, M.; "Microbiology of apical periodontisis in Essential Endodontology: Prevention and Treatment of Apical Periodontitis", Orstavik, D., Pitt Ford, T.R., Eds.; Blackwell Science: Oxford, pp. 106-130, (1998).
D'Aquino, R., Graziano, A., Sampaolesi, M.,. Laino, G., Pirozzi, G., De, R.A., Papaccio, G; "Human postnatal dental pulp cells co-differentiate into osteoblasts and endotheliocytes: a pivotal synergy leading to adult bone tissue formation," Cell Death. Differ. 14(6):1162-1171 (2007).
Das, S., Das, A.K., and Murphy, R.A.: "Experimental apexigenesis in baboons," Endod. Dent. Traumatol. 13:31-35 (1997).
Derringer, K.A., Linden, R.W.; "Angiogenic growth factors released in human dental pulp following orthodonitc force," Arch. Oral Biol. 48(4):285-291 (2003).
Derringer, K.A., Linden, R.W.; "Enhanced angiogenesis induced by diffusible angiogenic growth factors released from human dental pulp explants of orthodontically moved teeth," Eur. J. Orthod. 20(4):357-367 (1998).
Derringer, K.A., Linden, R.W.; "Vascular endothelial growth factor, fibroblast growth factor 2, platelet derived growth factor and transforming growth factor beta released in human dental pulp following orthodontic force," Arch. Oral Biol. 49(8):631-641 (2004).
Dikovsky, D., Bianco-Peled, H., Seliktar, D.; "The effect of structural alterations of PEG-fibrinogen hydrogel scaffolds on 3-D cellular morphology and cellular migration," Biomaterials. 27:(8)1496-1506 (2006).
Eanes, E.D., "Mixed Phospholipid Liposome Calcification," Bone Miner. 17(2):269-272 (1992).
Eanes, E.D., and Hailer, A.W., "Liposome-Mediated Calcium Phosphate Formation in Metastable Solutions," Calcif. Tissue. Int. 37(4):390-394 (1985).
Eanes, E.D., Hailer, A.W., and Costa, J.L., "Calcium Phosphate Formation in Aqueous Suspensions of Multilamellar Liposomes," Calicf. Tissue Int. 36(4):421-430 (1984).
Edwards et al., "Gene-enhanced tissue engineering for dental hard tissue regeneration: (2) dentin-pulp and periodontal regeneration," Head Face Med. 2:1-9 (2006).
Elbert, D.L, Hubbell, J.A.; "Conjugate addition reactions combined with free-radical cross-linking for the design of materials for tissue engineering," Biomacromolecules. 2(2):430-441 (2000).
Elisseeff, J., et al., "Transdermal Photopolymerization for Minimally Invasive Implantation," Proc. Natl. Acad. Sci. 96(6):3104-3107.
Elisseeff, J., Mcintosh, W., Anseth, K., Riley, S., Ragan, P., Langer, R.; "Photoencapsulation of chondrocytes in poly(ethylene oxide)-based semi-interpenetrating networks," J. Biomed. Mater. Res. 51(2):164-171 (2000).
Etienne, O. et al., "Degradability of polysaccharides multilayer films in the oral environment: an in vitro and in vivo study," Biomacromolecules. 6(2):726-733 (2005).
Ettel, R.G., et al., "Porous Hydroxyapatite Grafts in Chronic Subcrestal Periodontal Defects in Rhesus Monkeys: A Histological Invesitgation," J. Periodontol 60(6):342-351 (1989).
Extended European Search Report dated Aug. 29, 2013 in connection with European Application No. 08841018.8.
Fan, Hongbin, et al., "Enhanced Differentiation of Mesenchymal Stem Cells Co-cultured with Ligament Fibroblasts on Gelatin/Silk Fibroin Hybrid Scaffold," Biomaterials. 29(8):1017-1027 (2008).
Fong et al., "The Crowning Achievement: Getting to the Root of the Problem," J. Dent. Educ. 69(5):555-570 (2005).
Friedman, S.: "Treatment outcome and prognosis of endodontic therapy," in Orstavik, D. and Pitt Ford, T.R., (eds.): Essential Endodontology: Prevention and Treatment of Apical Periodontitis. Oxford, Blackwell Science, pp. 367-401 (1998).
Fuks, A.B., et al., "Pulp response to collagen and glutaraldehyde in pulpotomized primary teeth of baboons," Pediatr. Dent. 13:142-150 (1991).
Fuks, A.B., Michaeli, Y., Sofer-Saks, B., Shoshan, S.; "Enriched collagen solution as a pulp dressing in pulpotomized teeth in monkeys," Pediatr. Dent. 6:243-247 (1984).
Gao, Kai, et al., "Anterior Cruciate Ligament Reconstruction with LARS Artificial Ligament: A Multicenter Study with 3-to 5-Year Follow-Up," Arthroscopy. 26(4):515-523 (2010).
Gay, C.V., Schraer, H., and Hargest, T.E., "Ultrastructure of Matrix Vesicles and Mineral in Unfixed Embryonic Bone," Metab. Bone Dis. Relat. Res. 1(2):105-108 (1978).
Giannoudis, P.V., Dinopoulos, H., and Tsiridis, E., "Bone Substitutes: An Update," Injury, Int. J. Care Injured 36S:S20-S27 (2005).

(56) References Cited

OTHER PUBLICATIONS

Goldberg, M., Smith, A.J.; "Cells and extracellular matrices of dentin and pulp: A biological basis for repair and tissue engineering," Crit. Rev. Oral Biol. Med. 15(1):13-27 (2004).

Grando, M.L., Westphalen, B.L., de Figueiredo, J.A., Nor, J.E., de Araujo, F.B., Fossati, A.C.; "Vascular endothelial growth factor and its relationship with the dental pulp," J. Endod. 33(5):524-530 (2007).

Gronthos, S., Brahim, J., Li, W., Fisher, L.W., Gherman, N., Boyde, A., DenBesten, P., Robey, P.G., Shi, S.; "Stem cell properties of human dental pulp stem cells," J. Dent. Res. 81:531-535 (2002).

Gronthos, S., Mankani, M., Brahim, J., Robey, P.G., Shi, S.; "Postnatal human dental pulp stem cells (DPSCs) in vitro and in vivo," PNAS. 97:13625-13630 (2000).

Güven, Günseli, et al., "Co-Expression of Cyclooxygenase-2 and Vascular Endothelial Growth Factor in Inflamed Human Pulp: An Immunohistochemical Study," J. Endod. 33(1):18-20 (2007).

Hao, J. et al., "Mineralized nodule formation by human dental papilla cells in culture," Eur. J. Oral Sci. 105:318-324 (1997).

Hargreaves, K.M., Goodis, H.E.; Seltzer and Bender's: Dental Pulp. Chicago, Quintessence Publishing Co. Inc., 2002.

Hasselgren G., Larsson A., Rundquist L.; "Pulpal status following autogenous transplantation of fully developed maxillary canines," Oral Surg. 44:106-112 (1977).

He, Huixia, et al., "Biocompatibility and Osteogenic Capacity of Periodontal Ligament Stem Cells on nHAC/PLA and HA/TCP Scaffolds," J. Biomater. Sci. Polym. Ed. 22(1-3):179-194 (2011).

Henneman, S., Von Den Hoff, J.W., and Maltha, J.C., "Mechanobiology of Tooth Movement," Eur. J. Orthod. 30(3):299-306 (2008).

Herrick, S., Blanc-Brude, O., Gray, A., Laurent, G., "Fibrinogen," Int. J. Biochem. Cell Biol. 31(7):741-746 (1999).

Ho, Sunita P., et al., "The Biomechanical Characteristics of the Bone-Periodontal Ligament-Cementum Complex," Biomaterials. 31(25):6635-6646 (2010).

Ho, Sunita P., et al., "The Tooth Attachment Mechanism Defined by Structure, Chemical Composition and Mechanical Properties of Collagen Fibers in the Periodontium," Biomaterials. 28(35):5238-5245 (2005).

Hong, L., and Mao, J.J., "Tissue-Engineered Rabbit Cranial Suture from Autologous Fibroblasts and BMP2," J. Dent. Res. 83(10):751-756.

Horiuchi, Keisuke, et al., "Identification and Characterization of a Novel Protein Periostin, with Restricted Expression to Periosteum and Periodontal Ligament and Increased Expression by Transforming Growth Factor β," J. Bone. Miner. Res. 14(7):1239-1249 (1999).

Horsted P., Sandergaard B., Thylstrup A., El Attar K., Fejerskov O.; "A retrospective study of direct pulp capping with calcium hydroxide compounds," Endo. Dent. Traumatol: 1:29-34 (1985).

Huang et al., "A Review on Polymer Nanofibers by Electrospinning and Their Applications in Nanocomposites," Compos. Sci. Technol. 63(15):2223-2253.

Huang et al., "The Effect of Tetracycline Embedded Liposomes on the Mineralization of Rat Osteoblast-Enriched Cultures," The IADR/AADR/CADR 80th General Session 2002 (Abstract).

Huang, J.S., et al., "Effect of Liposomes on Mineralization in Rat Osteoblast-Enriched Cultures," Kaohsiung J. Med. Sci. 15(4):187-194 (1999) (Abstract only).

Ierardi, D.F., et al., "Erythrocyte Ghost Cell-Alkaline Phosphatase: Construction and Characterization of a Vesicular System for Use in Biomineralization Studies," Biochem. Biophys. Acta. 1567(1-2):183-192 (2002).

Iohara et al., "Dentin Regeneration by Dental Pulp Stem Cell Therapy with Recombinant Human Bone Morphogenetic Protein 2," J. Dental Res., 83(8):590-595 (2004).

Jackson, I.T., and Yavuzer, R., "Hydroxyapatite Cement: An Alternative for Craniofacial Skeletal Contour Refinements," Br. J. Plast. Surg. 53(1):24-29 (2000).

Jepsen, S., Albers, H.K., Fleiner, B., Tucker, M., Rueger, D.; "Recombinant human osteogenic protein-1 indnuces dentin formations: an experimental study in miniature swine," J. Endod. 23:378 (1997).

Kaigler, D. et al., "Tissue engineering's impact on Dentistry," J. Dent. Educ. 65:456-462(2001).

Katti et al., "Bioresorbable Nanofiber-Based Systems for Wound Healing and Drug Delivery: Optimization of Fabrication Parameters," J. Biomed. Mater. Res. B. Appl. Biomater. 70:286-296 (2004).

Kay, M.I., Young, R.A., and Posner, A.S., "Crystal Structure of Hydroxyapatite," Nature. 204:1050-1052 (1964) (Abstract).

Khanarian, et al., "A functional agarose-hydroxyapatite scaffold for osteochondral interface regeneration," Biomaterials. 33(21):5247-5258 (2012).

Kim, I.J., et al., "Extracellular Signal-Regulated Kinases Regulate Dendritic Growth in Rat Sympathetic Neurons," J. Neurosci. 24(13):3304-3312 (2004).

Kirsch, T., et al., "The Roles of Annexins and Type II and X Collagen in Matrix Vesicle-Mediated Mineralization of rowth Plate Cartilage," J. Biol. Chem. 275(45):35577-35583 (2000).

Kishi, Y., Takahashi, K.; "Change of Vascular Architecture of Dental Pulp with Growth" in Dynamic Aspects of Dental Pulp, Inoki, R., Kuda, T., Olgart, L., Eds.; Chapman and Hall: London, pp. 97-129 (1995).

Klein et al., "Loss of Sprouty2 or Sprouty4 Leads to Development of Supernumerary Teeth by Modulating FGF Signaling," Cost Action B23 Oral Facial Development and Regeneration, Joint Meeting of the Working Group 1-4 and the Management Committee. 47(2):13 (2006).

Kling, M., Cvek, M., and Mejare, I.: "Rate and predictability of pulp revascularization in therapeutically reimplanted permanent incisors," Endod. Dent. Traumatol. 2:83-89 (1986).

Klokkevold, P.R., Fukayama, H., Sung, E.C., Bertolami, C.N.; "The effect of chitosan (poly-N-acetyl glucosamine) on lingual hemostasis in heparinized rabbits," J. Oral Maxillofac. Surg. 57(1):49-52 (1999).

Knezevic, V., Sim, A.J., Borg, T.K., Holmes, J.W.; "Isotonic biaxial loading of fibroblast-populated collagen gels: a versatile, low-cost system for the study of mochanobiology." Biomech. Model Mechanobiol. 1(1):59-67 (2002).

Kontonasaki, E., et al., "Attachment and Proliferation of Human Periodontal Ligament Fibroblasts on Bioactive Glass Modified Ceramics.," J. Oral. Rehabil. 34(1):57-67 (2007).

Koran et al., "Apparent viscosity of materials used for making edentulous impressions," J. Amer. Dent. Assoc. 95:75-79 (1977).

Kwei, et al., "Nanofiber Alignment Regulates Adhesion and Integrin Expression of Human Mesenchymal Stem Cells and Tendon Fibroblasts," Proceedings of the 2010 IEEE—36th Annual Northeast Bioengineering Conference, Mar. 26-Mar. 28, 2010 p. 1-2.

Lalani, Z., et al., "Spatial and Temporal Lotalization of FGF-2 and VEGF in Healing Tooth Extraction Sockets in a Rabbit Model," J. Oral. Maxiofac. Surg. 63(10):1500-1508 (2005).

Landesberg R., Roy M., Glickman R.S.; "Quantification of growth factor levels using a simplified method of platelet-rich plasma gel preparation," J. Oral Maxillofac. Surg. 58(3):297-300 (2000).

Langer, R. and Vacanti, J.P., "Tissue Engineering," Science. 260:920-926 (1993).

Laurencin, et al., "Tissue Engineering: Orthopedic Applications," Annu. Rev. Biomed. Eng. 1:19-46 (1999).

Leong, N.L., Jiang, J., and Lu., H.H., "Polymer-Ceramic Composite Scaffold Induces Osteogenic Differentiation of Human Mesenchymal Stem Cells," Conf. Proc. IEEE. Eng. Med. Biol. Soc. 1:2651-2654 (2006).

Li, H., et al., "Hydroxyapatite Coating Enhances Polyethylene Terephthalate Artificial Ligament Graft Osseointegration in the Bone Tunnel," Int. Orthop. 35(10):1561-1567 (2011).

Liao, F., et al., "A Novel Bioactive Three-Dimensional B-Tricalcium Phosphate/Chitosan Scaffold for Periodontal Tissue Engineering," J. Mater. Sci. Mater. Med. 21(2):489-496 (2010).

Liao, S., et al., "Processing Nanoengineered Scaffolds Through Electrospinning and Mineralization Suitable for Biomimetic Bone Tissue Engineering," J. Mech. Behav. Biomed. Mater. 1(3):252-260 (2008).

(56) References Cited

OTHER PUBLICATIONS

Liao, S.S., et al. "Hierarchically Biomimetic Bone Scaffold Materials: Nano-HA/Collagen/PLA Composite," J. Biomed. Mater. Res. B Appl. Biomater. 69(2):158-165 (2004).
Lovschall, H., et al., "Pulp-Capping with Recombinant Human Insulin-Like Growth Factor I (rhIGF-I) in Rat Molars," Adv. Dent. Res. 15(1):108-112 (2001).
Lu et al., "Three-dimensional, bioactive, biodegradable, polymer-bioactive glass composite scaffolds with improved mechanical properties support collagen synthesis and mineralization of human osteoblast-like cells in vitro," J. Biomed. Matls. Res. 64A(3):465-474 (2003).
Lu, H. et al., "In vitro bone formation using muscle-derived cells: a new paradigm for bone tissue engineering using polymer-bone morphogenetic protein matrices," Biochem. Biophys. Res. Commun. 305(4):882-889 (2003).
Lu, H., et al., "Polymer-Bioactive Glass Composite Scaffold for Bone Tissue Engineering: Matrix Design and in Vitro Evaluations," Bioengineering conference ASME. 50:693-694 (2001).
Lu, H., Jiang, J., Tang, A., Hung, C. T., Guo, X.E.; "Development of Controlled Heterogeneity on a Polymer-Ceramic Hydrogel Scaffold for Osteochondral Repair," Bioceramics. 17 (Key Engineering Materials vols. 284-286), 607-610 (2005).
Lutolf, M.P., Hubbell, J.A.; "Synthesis and physiochemical characterization of end-linked poly(ethylene glycol)-co-peptide hydrogels formed by Michael-type addition," Biomacromolecules. 4(3):713-722 (2003).
Lynch, S.E., et al., "A Combination of Platelet-Derived and Insulin-Like Growth Factors Enhances Periodontal Regeneration," J. Clin. Periodontol. 16(8):545-548 (1989).
Ma, L., Gao, C., Mao, Z., Zhou, J., Shen, J., Hu, X., Han, C.; "Collagen/chitosan porous scaffolds with improved biostability for skin tissue engineering," Biomaterials. 24(26):4833-4841 (2003).
Ma, Z., et al., "Grafting of Gelatin on Electrospun Poly(caprolactone) Nanofibers to Improve Endothelial Cell Spreading and Proliferation and to Control Cell Orientation," Tissue Eng. 11(7-8):1149-1158 (2005).
Magloire H.; Joffre A., Bleicher F.; "An in vitro model of human dental pulp repair," J Dent. Res. 75(12):1971-8 (1996).
Majeska, R.J., and Wuthier, R.E., "Studies on Matrix Vesicles Isolated from Chick Epiphyseal Cartilage Association of Pyrophosphatase and ATPase Activities with Alkaline Phosphatase," Biochim. Biophys. Acta. 391(1):51-60 (1975).
Mao, J.J. et al., "Craniofacial Tissue Engineering by Stem Cells," J. Dent. Res. 85(11):966-979 (2006).
Mathieu, S., El-Battari, A., Dejou, J., About, I.; "Role of injured endothelial cells in the recruitment of human pulp cells," Arch. Oral Biol. 50(2):109-113 (2005).
Mattuella, et al., "Vascular Endothelial Growth Factor and Its Relationship with the Dental Pulp," J. Endod. 33(5):524-50 (2007).
Mauck, R.L. et al., "Functional tissue engineering of articular cartilage through dynamic loading of chondrocyte-seeded agarose gels," J. Biomech. Eng. 122:252-260 (2000).
Mejare, I. and Cvek, M.; "Partial pulpotomy in young permanent teeth with deep cariuos lesions," Endod. Dent. Traumatol. 9:238-242 (1993).
Mesaros, S.V. and Trope, M.; "Revascularization of traumatized teeth assessed by laser Doppler flowmetry: case report," Endod. Dent. Traumatol. 13:24-30 (1997).
Messersmith, P.B., and Starke, S., "Thermally Triggered Calcium Phosphate Formation from Calcium-Loaded Liposomes," Chem. Mater. 10(1):117-121 (1998).
Messersmith, P.B., Vallabhaneni, S., and Nguyen, "Preparation of Calcium-Loaded Liposomes and Their Use in Calcium Phosphate Formation," Chem. Mater. 10(1):109-116 (1998).
Michel, M., et al., "Giant Liposome Microreactors for Controlled Production of Calcium Phosphate Crystals," Langmuir. 20(15):6127-6133 (2004).
Mikos, A.G., et al., "Engineering Complex Tissues," Tissue Eng. 12(12):3307-3339.

Mjor, I.A., Heyeraas, K.J.; "Pulp-Dentin and Periodontal Anatomy and Physiology," In Essential Endodontology, Orstavik, D., Pitt Ford, T.R., Eds.; Blackwell Science: New York, pp. 9-41 (1998).
Moioli, E.K., et al., "Sustained Release of TGFβ3 from PLGA Microspheres and Its Effect on Early Osteogenic Differentiation of Human Mesenchymal Stem Cells," Tissue Eng. 12(3):537-546 (2006).
Mooney, D.J., et al., "Engineering dental pulp-like tissue in vitro," Biotechnol. Prog. 12:865-868 (1996).
Moreau, J.E., et al., "Sequential Biochemical and Mechanical Stimulation," Tissue Eng. Part A. 14(7):1161-1172 (2008).
Mori, T.; Okumura, M.; Matsuura, M.; Ueno, K.; Tokura, S.; Okamoto, Y.; Minami, S.; Fujinaga, T. Effects of chitin and its derivates on the proliferation and cytokine production of fibroblasts in vitro. Biomaterials. 18(13):947-951 (1997).
Murphy, William L., and Messersmith, Phillip B., "Compartmental Control of Mineral Formation: Adaptation of a Biomineralization Strategy for Biomedical Use," Polyhedron. 19(3):357-363 (2000).
Murphy, William L., et al. "Sustained Release of Vascular Endothelial Growth Factor from Mineralized Poly (lactide-co-glycolide) Scaffolds for Tissue Engineering," Biomaterials. 21(24):2521-2527 (2000).
Murray et al., "Analysis of Pulpal Reactions to Restorative Prodedures, Materials, Pulp Capping, and Future Therapies," Crit. Rev. Oral. Biol. Med. 13(6):509-520 (2002).
Murray, M.M., Spindler, K.P., Ballard, P., Welch, T.P., Zurakowski, D., Nanney, L.B.; "Enhanced histologic repair in a central wound in the anterior cruciate ligament with a collagen-platelet-rich plasma scaffold," J. Orthop. Res. 25(8):1007-17 (2007).
Murray, M.M., Spindler, K.P., Devin, C., Snyder, B.S., Muller, J., Takahashi, M., Ballard, P., Nanney, L.B., Zurakowski, D.; "Use of a collagen-platelet rich plasma scaffold to stimulate healing of a central defect in the canine ACL," J. Orthop. Res. 24(4):820-830 (2006).
Muzzarelli et al., "Osteoconduction exerted by methylpyrrolidinone chitosan used in dental surgery," Biomaterials. 14(1):39-43 (1993).
Muzzarelli, R., Biagini, G., Pugnaloni, A., Filippini, O., Baldassarre, V., Castaldini, C., Rizzoli, C.; "Reconstruction of parodontal tissue with chitosan," Biomaterials. 10(9):598-603 (1989).
Myers, W.C. and Fountain, S.B.; "Dental pulp regeneration aided by blood and blood substitutes after experimentally induced periapical infection," Oral. Surg. 37:441-450 (1974).
Nakamura, Yukio, et al., "Temporal and Spatial Expression Profiles of BMP Receptors and Noggin during BMP-2-Induced Ectopic Bone Formation," J. Bone Miner. Res. 18(10):1854-1862 (2003).
Nakashima, M. et al., "Induction of dental pulp stem cell differentiation into odontoblasts by electroporation-mediated gene delivery of growth/differentiation factor 11 (Gdf11)," Gene Ther. 9:814-818 (2002).
Nakashima, M., "Induction of dentine in amputated pulp of dogs by recombinant human bone morphogenetic proteins-2 and -4 with collagen matrix," Arch. Oral Biol. 39:1085-1089 (1994).
Nakashima, M., "Establishment of primary cultures of pulp cells from bovine permanent incisors," Arch. Oral Biol. 36:655-663 (1991).
Nakishma, M., and Akamine, A., "The Application of Tissue Engineeering to Regeneration of Pulp and Dentin in Endodontics," J. Endod. 31(10): 711-718 (2005).
Nakishma, M., and Reddi, A.H., "The Application of Bone Morphogenetic Proteins to Dental Tissue Engineering," Nat. Biotechnol. 21(9):1025-1032 (2003).
Nevins, A., Finkelstein, F., Laporta, R., and Borden, B.G.; "Induction of hard tissue into pulpless open-apex teeth usinq collagen-calcium phosphate gel," J. Endod. 4:76-81 (1978).
Nevins, A., Finkelstein, F., Laporta, R., Borden, B.G., and Moodnik, R.: "Formation of mineralized scar tissue induced by implants containing collagen-calcium phosphate gel," J. Endod. 1:303-309 (1975).
Nevins, A.J., Finkelstein, F., Borden, B.G., and Laporta, R.: "Revitalization of pulpless open apex teeth in rhesus monkeys, using collagen-calcium phosphate gel," J. Endod. 2:159-16 (1976).
Nevins, A.J., LaPorta, R.F., Borden, B.G., and Spangberg, L.S.: "Pulpotomy and partial pulpectomy procedures in monkey teeth

(56) References Cited

OTHER PUBLICATIONS using cross-linked collagen-calcium phosphate gel," Oral Surg. Oral Med. Oral Pathol. 49:360-365 (1980).
Nguyen, K.T., West, J.L.; "Photopolymerizable hydrogels for tissue engineering applications," Biomaterials. 23(22):4307-4314 (2002).
Nishimura, K., Nishimura, S., Seo, H., Nishi, N., Tokura, S., Azuma, I.; "Effect of multiporous microspheres derived trom chitin and partially deacetylated chitin on the activation of mouse peritoneal macrophages," Vaccine. 5:(2)136-140 (1987).
Nyborg, H., "Healing processes in the pulp on capping; a morphologic study; experiments on surgical lesions of the pulp in dog and man," Acta Odontol. Scand. 13(suppl.16):1-130 (1995).
O. Sarig-Nadir et al., "Laser Photoablation of Guidance Microchannels into Hydrogels Directs Cell Growth in Three Dimensions," Biophy. J., vol. 96, pp. 4743-4752 (2009).
Okiji, T., "Pulp as a connective tissue," In Hargreaves, K.M. and Goodis, H.E., (eds.): Seltzer and Bender's: Dental Pulp. Chicago, Quintessence Publishing Co, Inc., 2002.
Osborn, J.F., and Newesely, H., "The Material Science of Calcium Phosphate Ceramics," Biomaterials. 1(2):108-111 (1980).
Ozawa M., Ikeda H., Suda H.; "The effect of pulpward pressure on the response to 50% lidocaine (lignocaine) applied to exposed dentine in cats," Arch. Oral Biol. 47(4):333-6 (2002).
Park, D.J., Choi, B.H., Zhu, S.J., Huh, J.Y., Kim, B.Y., Lee, S.H.; "Injectable bone using chitosanalginate gel/Mesenchymal stem cells/BMP-2 composites," J. Craniomaxillofac. Surg. 33:(1)50-4 (2005).
Park, H., et al., "Delivery of TGF-β1 and Chondrocytes via Injectable, Biodegradable Hydrogels for Cartilage Tissue Engineering Applications," Biomaterials. 26(34):7095-7103 (2005).
Park, J.S., Choi, S.H., Moon, I.S., Cho, K.S., Chai, J.K., Kim, C.K.; "Eight-week histological analysis on the effect of chitosan on surgically created one-wall intrabony defects in beagle dogs," J. Clin. Periodontol. 30(5):443-453 (2003).
PCT International Preliminary Report on Patentability dated Dec. 11, 2009 in connection with PCT Application No. PCT/US2008/007323, international filing date Jun. 11, 2008.
PCT International Preliminary Report on Patentability dated Dec. 11, 2009 in connection with PCT Application No. PCT/US2008/007357, international filing date Jun. 11, 2008.
PCT International Preliminary Report on Patentability dated Feb. 24, 2009 in connection with PCT Application No. PCT/US2005/007010, international filing date Mar. 4, 2005.
PCT International Preliminary Report on Patentability dated Jun. 10, 2009 in connection with PCT Application No. PCT/US2007/025127, international filing date Dec. 6, 2007.
PCT International Preliminary Report on Patentability dated Jan. 10, 2013 in connection with PCT Application No. PCT/US2011/041391, international filing date Jun. 22, 2011.
PCT International Preliminary Report on Patentability dated Jan. 24, 2013 in connection with PCT/US2011/043687, international filing date Jul. 12, 2011.
PCT International Preliminary Report on Patentability dated Oct. 22, 2015 1n connection with PCT Application No. PCT/US2014/033843, international filing date Apr. 11, 2014.
PCT International Preliminary Report on Patentability dated Sep. 5, 2006 in connection with PCT Application No. PCT/US2005/007129, international filing date Mar. 4, 2005.
PCT International Search Report dated Aug. 29, 2014 in connection with PCT Application No. PCT/US2014/033866, international filing date Apr. 11, 2014.
PCT International Search Report dated Aug. 29, 2014 in connection with PCT Application No. PCT/US2014/033843, international filing date Apr. 11, 2014.
PCT International Search Report dated Dec. 8, 2008 in connection with PCT Application No. PCT/US2008/007323, international filing date Jun. 11, 2008.
PCT International Search Report dated Feb. 14, 2006 in connection with PCT Application No. PCT/US2005/007129, international filing date Mar. 4, 2005.
PCT International Search Report dated Feb. 17, 2010 in connection with PCT Application No. PCT/US2009/006453, international filing date Dec. 8, 2009.
PCT International Search Report dated Jan. 2, 2009 in connection with PCT Application No. PCT/0S2008/001011.
PCT Tnternational Search Report dated Jan. 5, 2012 in connection with PCT Application No. PCT/US2011/047739, international filing date Aug. 15, 2011.
PCT International Search Report dated Jan. 6, 2009 in connection with PCT Application No. PCT/US2008/010985, international filing date Sep. 22, 2008.
PCT International Search Report dated Jan. 9, 2012 in connection with PCT Application No. PCT/US2011/041391, international filing date Jun. 22, 2011.
PCT International Search Report dated Jan. 9, 2012 in connection with PCT Application No. PCT/US2011/043687, international filing date Jul. 12, 2011.
PCT International Search Report dated Jul. 14, 2008 in connection with PCT Application No. PCT/US2005/007010, international filing date Mar. 4, 2005.
PCT International Search Report dated Jul. 19, 2008 in connection with PCT Application No. PCT/US2008/001889, international filing date Feb. 12, 2000.
PCT International Search Report dated Jun. 17, 2008 in connection with PCT Application No. PCT/US2007/025127, international filing date Dec. 6, 2007.
PCT International Search Report dated Mar. 3, 2009 in connection with PCT Application No. PCT/US2008/007485, international filing date Jun. 11, 2008.
PCT International Search Report dated Oct. 14, 2008 in connection with PCT Application No. PCT/US2008/007357, international filing date Jun. 11, 2008.
PCT International Search Report dated Oct. 16, 2007 in connection with PCT Application No. PCT/US2006/015860.
Peters et al., "Engineering vascular networks in porous polymer matrices," J. Biomed. Mater. Res. 60(4):668-678 (2002).
Rabea, E.I., Badawy, M.E., Stevens, C.V., Smagghe, C., Steurbaut, W.; "Chitosan as antimicrobial agent: Applications and mode of action," Biomacromolecules. 4(6):1457-1465 (2003).
Ranly, D.M. and Garcia-Godoy, F., "Current and potential pulp therapies for primary and young permanent teeth," J. Dent. 28(3):153-61 (2000).
Reddy, G.K., and Enwemeka, C.S., "A Simplified Method for the Analysis of Hydroxyproline in Biological Tissues," Clin. Biochem. 29(3):225-229 (1996).
Register, T.C., et al., "Roles of Alkaline Phosphatase and Labile Internal Mineral in Matrix Vesicle-Mediated Calcification. Effect of Selective Release of Membrane-Bound Alkaline Phosphatase and Treatment with Isosmotic pH 6 Buffer," J. Biol. Chem. 261(20):9354-9360 (1986).
Reisbick, M.H., "Effect of Viscosity on the Accuracy and Stability of Elastic Impression Materials," J. Dent. Res. 52:407-411 (1973).
Reneker, D.H., and Chun, I., "Nanometre Diameter Fibres of Polymer, Produced by Electrospinning," Nanotechnology. 7(3):216 (1996).
Richardson et al., "Polymeric system for dual growth factor delivery," Nat. Biotechnol. 19:1029-1034 (2001).
Rudan, S.B., et al., "Characterization of a Human Osteosarcoma Cell Line (Saos-2) with Osteoblastic Properties," Cancer. Res. 47(18):4961-4966 (1987).
Roeder, B.A., Kokini, K., Sturgis, J.E., Robinson, J.P., and Voytik-Harbin, S.L.; "Tensile mechanical properties of three-dimensional type I collagen extracellular matrices with varied microstructure," J. Biomed. Eng. 124:214-222 (2002).
Rungvechvuttivittaya, S., et al., "Responses of macrophage-associated antigen-expressing cells in the dental pulp of rat molars to experimental tooth replantation," Arch. Oral Biol. 43:701-710 (1998).
Rutherford, B. et al., "A new biological approach to vital pulp therapy," Crit. Rev. Oral Biol. Med. 6:218-229 (1995).
Rutherford, R.B. et al., "Treatment of inflamed ferret dental pulps with recombinant bone morphogenetic protein-7," Eur. J. Oral Sci. 108:202-206 (2000).

(56) References Cited

OTHER PUBLICATIONS

Rutherford, R.B., "BMP-7 gene transfer to inflamed ferret dental pulps," Eur. J. Oral Sci. 109:422-424 (2001).
Salani, D., Taraboletti, G., Rosano, L., Di, C., V, Barsotti, P., Giavazzi, R., Bagnato, A.; "Endothelin-1 induces an angiogenic phenotype in cultured endothelial cells and stimulates neovascularization in vivo," Am. J. Pathol. 157(5):1703-1711 (2000).
Salvi, G.E., et al., "Clinical Evaluation of Root Filled Teeth Restored with or without Post-and-Core Systems in a Specialist Practice Setting," Int. End. J. 40(3):209-215 (2007).
Sapelli, P., Baldassare, V., Muzzarelli, R., Emanuelli, M.; "Chitosan in Dentistry," In Chitin in Nature and Technology, pp. 507-512, 1986.
Sarasam, A., Madihally, S.V.; "Characterization of chitosan-polycaprolactone blends for tissue engineering applications," Biomaterials. 26(27):5500-5508 (2005).
Sarig-Nadir, O., et al., "Laser Photoablation of Guidance Microchannels into Hydrogels Directs Cell Growth in Three Dimensions," Biophys. J. 96(11):4743-4752 (2009).
Sarraf, C.E., Otto, W.R., and Eastwood, M., "In Vitro Mesenchymal Stem Cell Differentiation after Mechanical Stimulation," Cell Prolif. 44(1):99-108 (2011).
Seliktar, D., "Extracellular stimulation in tissue engineering," Ann. N.Y. Acad. Sci. 1047:386-394 (2005).
Seo, Byoung-Moo, et al., "Investigation of Multipotent Postnatal Stem Cells from Human Periodontal Ligament," Lancet. 364(9429):149-155) (2004).
Shao, H.J., ct al., "Designing a Three-Dimensional Expanded Polytetrafluoroethylene-Poly (Lactic-Co-Glycolic Acid) Scaffold for Tissue Engineering," Artif. Organs. 33(4):309-317 (2009).
Shay, K., "Infectious Complications of Dental and Periodontal Diseases in the Elderly Population," Clin. Infect. Dis. 34(9):1215-1223 (2002).
Sherwood, J.K., et al., "A Three-Dimensional Osteochondral Composite Scaffold for Articular Cartilage Repair," Biomaterials. 23(24):4739-4751 (2002).
Shor, L., et al., "Fabrication of Three-Dimensional Polycaprolactone/Hydroxyapatite Tissue Scaffolds and Osteoblast-Scaffold Interactions in Vitro," Biomaterials. 28(35):5291-5297 (2007).
Six, N. et al., "Differential repair responses in the coronal and radicular areas of the exposed rat molar pulp induced by recombinant human bone morphogenetic protein 7 (osteogenic protein 1)," Arch. Oral Biol. 47:177-187 (2002).
Six, N. et al., "Osteogenic proteins (bone sialoprotein and bone morphogenetic protein-7) and dental pulp mineralization," J. Mater. Sci. Mater. Med. 13:225-232 (2002).
Sjogren, U., Hagglund, B., Sundqvist, G., and Wing, K.: "Factors affecting the long-term results of endodontic treatment," J. Endod. 16:498-504 (1990).
Skoglund, A. and Hasselgren, G., "Tissue changes in immature dog teeth autotransplanted to surgically prepared sockets," Oral Surg. Oral Med. Oral Pathol. 74:789-95 (1992).
Skoglund, A. and Tronstad, L., "Pulpal changes in replanted and autotransplanted immature teeth of dogs," J. Ended. 7(7):309-316 (1981).
Skoglund, A., "Pulpal changes in replanted and autotransplanted apicoectomized mature teeth of dogs," Int. J. Oral Surg. 10:111-121 (1981).
Skoglund, A., "Vascular changes in replanted and autotransplanted apicoectomized mature teeth of dogs," Int. J. Oral Surg. 10:100-110 (1981).
Skoglund, A., Tronstad, L., and Wallenius, K.; "Pulpal survival in replanted and auto-transplanted apicoectomized mature teeth of dogs with prepared nutritional canals," Int. J. Oral Surg. 12:31-38 (1983).
Skoglund, A., Tronstad, L., and Wallenius, K; "A microangiographic study of vascular changes in replanted and autotransplanted teeth of young dogs," Oral Surg. Oral Med. Oral Pathol. 44:17-28 (1978).
Smith, C.S., Setchell, D.J., and Harty, F.J.; "Factors influencing the success of conventional root canal therapy—a five-year retrospective study," Int. Ended. J. 26:321-333 (1993).
Spalazzi, J.P. et al., "Mechanoactive Scaffold Induces Tendon Remodeling and Expression of Fibrocartilage Markers," Clin. Orthop. Relat. Res. 466(8):1938-1948 (2008).
Spalazzi, J.P., et al., "Development of Controlled Matrix Heterogeneity on a Triphasic Scaffold for Orthopedic Interface Tissue Engineering," Tissue Eng. 12(12):3497-3508 (2008).
Spalazzi, J.P., et al., "Osteoblast and Chondrocyte Interactions during Coculture on Scaffolds," IEEE Eng. Med. Biol. Mag. 22(5):27-34 (2003).
Spoerke, E.D., et al., "A Bioactive Titanium Foam Scaffold for Bone Repair," Acta. Biomater. 1(5):523-533(2005) (Abstract).
Stemgent Product Specification Sheet, Stemfactor™ FGF-Basic, Human Recombinant, 2012, 2 paqes.
Stoisch, M.S., and Mao, J.J., "Adipose Tissue Engineering from Human Adult Stem Cells: Clinical Implications in Plastic and Reconstructive Surgery," Plast. Reconstr. Surg. 119(1):71-83 (2007).
Stys, P.K., "General Mechanisms of Axonal Damage and Its Prevention," J. Neurol. Sci. 233(1-2):3-13 (2005) (Abstract).
Suda, H., Ikeda, H.; "The Circulation of the Pulp," In Seltzer and Bender's Dental Pulp, pp. 123-150 (2002).
Suh, J.K., Matthew, H.W.; Application of chitosan-based polysaccharide biomaterials in cartilage tissue engineering: a review. Biomaterials. 21(24):2589-2598 (2000).
Temenoff, J.S., Athanasiou, K.A., LeBaron, R.G., Mikos, A.G.; "Effect of poly( ethylene glycol) molecular weight on tensile and swelling properties of oligo(poly(ethylene glycol) fumarate) hydrogels for cartilage tissue engineering," J. Biomed. Mater. Res. 59(3):429-437 (2002).
Teng J., et al., "Human Pulpal Fibroblasts Cultured in Type I Collagen Gel for Dental Pulp Tissue Engineering," Proceedings of the Society for Biomaterials, 30th Annual meeting, p. 188 (2005).
Teng, J., et al., "Human Pulpal Fibroblasts Cultured in Type I Collagen Gel for Dental Pulp Tissue Engineering," Society for Biomaterials 30th Annual Meeting Transaction. 191(1):188 (2005).
Thibault, R.A., et al., "Osteogenic Differentiation of Mesenchymal Stem Cells on Pregenerated Extracellular Matrix Scaffolds in the Absence of Osteogenic Cell Culture Supplements," Tissue. Eng. Part A. 16(2):431-440 (2009).
Thresher et al., "The stress analysis of human teeth," J. Biomech. 6:443-449 (1973).
Toparli, M., Gokay, N., and Aksoy, T.: Analysis of a restored maxillary second premolar tooth by using three-dimensional finite element method. J. Oral Rehab. 76:157 (1999).
Tran-Hung, L., Mathieu, S., About, I.; "Role of human pulp fibroblasts in angiogenesis," J. Dent. Res. 85(9):819-823 (2006).
Tsai, J., and Kam, L., "Rigidity-Dependent Cross Talk between Integrin and Cadherin Signaling," Biophys. J. 96(6):L39-L41 (2009).
Tsay, R.C., Vo, J., Burke, A., Eisig, S.B., Lu, H.H., Landesberg, R.; "Differential growth factor retention by platelet-rich plasma composites," J. Oral Maxillofac. Surg. 63(4):521-528(2005).
Tziafas, D., Smith, A.J., and Leso, H.: "Designing new treatment strategies in vital pulp therapy," J. Dent. 28:77-92 (2000).
Van Amerongen, J.P. et al., "The concentration, extractability and characterization of collagen in human dental pulp," Arch. Oral Biol. 28:339-345 (1983).
Varghese, S., et al., "Chondroitin Sulfate Based Niches tor Chondrogenic Differentiation of Mesenchymal Stem Cells," Matrix. Biol. 27(1):12-21 (2008).
Venugopal, J.R., et al., "Nanobioengineered Electrospun Composite Nanofibers and Osteoblasts for Bone Regeneration," Artif. Organs. 32(5):388-397 (2008).
Vermilyea et al., "Rotational Viscometry of a Zinc Phosphate and a Zinc Polyacrylate Cement," J. Dent. Res. 56:762-767 (1977).
Verret, D.J., et al., "Hydroxyapatite Cement in Craniofacial Reconstruction," Otolaryrgol. Head Neck Surg. 133(6):897-899 (2005).
Vongsavan, N., Matthews, B.; The vascularity of dental pulp in cats. J. Dent. Res. 71(12):1913-1915 (1992).
Vunjak-Novakovic, G., et al., "Tissue Engineering of Ligaments," Annu. Rev. Biomed. Eng. 6(1):131-156 (2004).

(56) References Cited

OTHER PUBLICATIONS

Wang et al., "Multifunctional Chondroitin Sulphate for Cartilage Tissue-Biomaterial Integration," Nat. Matls. 6(5):385-392 (2007).
Wang, Y.H., et al., "Effects of BMP-7 on Mouse Tooth Mesenchyme and Chick Mandibular Mesenchyme," Dev. Dyn. 216(4-5):320-335 (1999).
Weiger, R., Axmann-Krcmar, D., and Lost, C.: Prognosis of conventional root canal treatment reconsidered. Endod. Dent. Traumatol. 14:1-9 (1998).
Weissman, et al., "Hydroxyapatite Cement to Repair Skull Base Defects: Radiologic Appearance," ANJR Am. J. Neuroradiol. 17(1):1569-1574 (1996).
Williams et al., "Orthodontic tooth movement analysed by the Finite Element Method," Biomaterials. 5:347-351 (1984).
Written Opinion of the International Search Authority dated Aug. 29, 2014, in connection with International Application No. PCT/US2014/033866, international filing date Apr. 11, 2014.
Written Opinion of the International Search Authority dated Feb. 14, 2006, in connection with PCT/US2005/007129, international filing date Mar. 4, 2005.
Written Opinion of the International Search Authority dated Feb. 17, 2010, in connection with International Application No. PCT/US2009/06453, international filing date Dec. 8, 2009.
Written Opinion of the International Search Authority dated Jan. 2, 2009, in connection with International Application No. PCT/US2008/081011, international filing date Oct. 23, 2008.
Written Opinion of the International Search Authority dated Jan. 6, 2009, in connection with PCT/US2008/010985, international filing date Sep. 22, 2008.
Written Opinion of the International Search Authority dated Jan. 2, 2009, in connection with International Application No. PCT/US2008/007323, international filing date Jun. 11, 2008.
Written Opinion of the International Search Authority dated Jan. 5, 2012, in connection with International Application No. PCT/US2011/047739, international filing date Aug. 15, 2011.
Written Opinion of the International Search Authority dated Jan. 9, 2012, in connection with International Application No. PCT/US2011/041391, international filing date Jun. 22, 2011.
Written Opinion of the International Search Authority dated Jan. 9, 2012, in connection with International Application No. PCT/US2011/043687, international filing date Jul. 12, 2011.
Written Opinion of the International Search Authority dated Jul. 14, 2008 in connection with International Application No. PCT/US2005/007010, international filing date Mar. 4, 2005.
Written Opinion of the International Search Authority dated Jun. 17, 2008 in connection with International Application No. PCT/US2007/025127, international filing date Dec. 6, 2007.
Witten Opinion of the International Search Authority dated Oct. 16, 2007, in connection with International Application No. PCT/US2006/015860, international filing date Apr. 28, 2008.
Written Opinion of the International Search Authority dated Oct. 14, 2008, in connection with International Application No. PCT/US2008/07357, international filing date Jun. 11, 2008.
Wu, W., and Nancollas, G.H., "Kinetics of Heterogeneous Nucleatior of Calcium Phosphates on Anatase and Rutile Surfaces," J. Colloid Interface Sci. l99(2):206-211 (1998).
Xie, J., et al., "Mechano-Active Scaffold Design Based on Microporous Poly (L-Lactide-Co-Epsilon-Caprolactone) for Articuial Cartliage Tissue Engineering: Dependence of Porosity on Compression Force-Applied Mechanical Behaviors," Tissue. Eng. 12 (3) 1449-458 (2006).
Yanpiset, K. and Trope, M.: "Pulp revascularization of replanted immature dog teeth after different treatment methods," Endod. Dent. Traumatol. 16:211-217 (2000).
Yanpiset, K., et al., "Efficacy of laser Doppler flowmetry for the diagnosis of revascularization of reimplanted immature doq teeth," Dent. Traumatol. 17:63-70 (2001).
Yin, Z., et al., "The Regulation of Tendon Stem Cell Differentiation by the Alignment of Nanofibers," Biomaterials. 31(8):2163-2175;.
Yoshimoto, H., et al., "A Biodegradable Nanofiber Scaffold by Electrospinning and Its Potential for Bone Tissue Engineering," Biomaterials. 24(12):2077-2082 (2003).
Young et al., "Tissue-Engineered Hybrid Tooth and Bone," Tissue Eng. 11(9-10):1599-610 (2005).
Young, C.S., "Tissue engineering of complex tooth structures on biodegradable polymer scaffolds," J. Dent. Res. 81:695-700 (2002).
Young, C.S., et al., "Tissue Engineering of Complex Tooth Structures on Biodegradable Polymer Scaffolds," J. Dent. Res. 81(10):695-700 (2002).
Zhang, J.Q., Nagata, K., and Iijima, T., "Scanning Electron Microscopy and Immunohistochemical Observations of the Vascular Nerve Plexuses in the Dental Pulp of Rat Incisor," Ant. Rec. 251(2):214-220 (1998).
Zhang, J.Q., Nagata, K., Iijima, T.; "Scanning electron microscopy and immunohistochemical observations of the vascular nerve plexuses in the dental pulp of rat incisor," Anal. Rec. 251(2):214-220 (1998).
Zheng-Ming Huang et al., "A review on polymer nanofibers by electrospinning and their applications in nanocomposites," Comp. Sci.Tech. 63:2223-2253 (2003).
Zhu, W., et al., "Viscoelastic Shear Properties of Articular Cartilage and the Effects of Glycosidase Treatments," J. Orthop. Res. 11(6):771-781 (1993).
Zhu, W., Mow, V.C., Koob, T.J., Eyre, D.R.; "Viscoelastic shear properties of articular cartilaqe and the effects of Glycosidase treatments," J. Orthop. Res. 11(6):771-781 (1993).
Zielinski, B.A., Aebischer, P.; "Chitosan as a matrix for mammalian cell encapsulation," Biomaterials. 15(13):1049-1056 (1994).
Zielinski, B.A., and Aebischer, P., "Chitosan as a Matrix for Mammalian Cell Encapsulation," Biomaterials. 15(13):1049-1056 (1994).
Zilberman, U., Mass, E., and Sarnat, H., "Partial Pulpotomy in Carious Permanent Molars," Am. J. Dent. 2(4):147 (1989).
Zilberman, U., Mass, E., and Sarnat, H.: "Partial pulpotomy in carious permanent molars," Am. J. Dent. 2:147-150 (1989).

* cited by examiner

*OVERTIME, ^ BETWEEN GROUP/DAY of this application with fibrinogen concentrations of 7.7, 8.5 and 9 mg/ml. FIG. 6A shows picrosirius staining of chondrocytes on scaffolds at days 1, 7, 21, 28 and 42. FIG. 6B is a bar graph of collagen content normalized to gel wet weight. FIG. 6C is a bar graph of the picrosirius stained area normalized to gel area.

METHODS FOR HOST CELL HOMING AND DENTAL PULP REGENERATION

This patent application is a continuation of U.S. application Ser. No. 14/783,778, filed Oct. 9, 2015, as a § 371 national stage of PCT International Application No. PCT/US2014/033866, filed Apr. 11, 2014, claiming the benefit of U.S. Provisional Application Ser. No. 61/811,433, filed Apr. 12, 2013, the contents of each of which are herein incorporated by reference in their entirety.

FIELD

The disclosed subject matter relates to hydrogel-based scaffolds useful in dental pulp tissue engineering and methods for use of these scaffolds in promoting pulp cell growth and biosynthesis, regulating cell infiltration into, migration and morphology within a hydrogel-based scaffold, in vitro methods for differentiation and expansion of stem cells, and promoting tooth vitality in subjects in need thereof.

BACKGROUND

Dental pulp is a soft non-mineralized connective tissue found at the core of the tooth, which is highly vascularized and innervated. Its extracellular matrix consists primarily of collagen type one and collagen type three. Dental pulp is an essential component of the tooth as it provides nutrients and sensitivity to dentin as well as new odontoblasts for dentin repair. Its primary function is to respond to dentinal injuries.

A dental pulp is susceptible to infection due to caries. Teeth with inflamed pulp are often treated by root canal therapy (RCT). Approximately 15 million root canal procedures are performed annually in the United States. This procedure includes pulp extirpation, followed by filling of the root canal which causes permanent loss of tooth vitality, halts root development in immature teeth and increases risk of infection, tooth fracture, and tooth lost.

Pulpotomy has been developed as an alternative approach to RCT. This procedure involves partial pulp removal which preserves pulp vitality. However, this procedure is uncommon as it is limited to nature of injury, young patient, and severity of pupal infection. Further, its long-term success rate is low.

Additional endodontic treatments currently under investigation include total tooth regeneration and pulp and dentin regeneration.

For total tooth regeneration, the goal is to regenerate replacement teeth in vivo utilizing biodegradable scaffolds with the aid of stem cells and stimuli. This approach is suitable for patients with total tooth loss For pulp and dentin regeneration, the goal is to utilize biodegradable scaffolds and stem cells to regenerate pulp.

SUMMARY

An aspect of this application relates to hydrogel-based, scaffolds for dental pulp tissue engineering. Scaffolds of this application comprise a biosynthetic hydrogel of polymer and fibrinogen. In one embodiment, fibrinogen is present in the scaffold at a concentration sufficient for promoting pulp cell growth and biosynthesis, regulating pulp cell infiltration into, migration and morphology, or both. Alternatively, or in addition, crosslinker content and/or PEG-diacrylate:fibrinogen ratio in the hydrogel-based scaffold can be modified.

Another aspect of this application relates to a method of promoting pulp cell growth and biosynthesis in a hydrogel-based scaffold. In this method, fibrinogen concentration, crosslinker content and/or PEG-diacrylate:fibrinogen ratio in the hydrogel-based scaffold is modulated to promote pulp cell growth and biosynthesis.

Another aspect of this application relates to a method of regulating cell infiltration into, migration and morphology within a hydrogel-based scaffold. In this method, fibrinogen concentration, crosslinker content and/or PEG-diacrylate:fibrinogen ratio in the hydrogel-based scaffold is modulated to regulate cell infiltration into, migration and morphology.

Another aspect of this application relates to an in vitro method for differentiation and expansion of stem cells into dental pulp cells. This method comprises culturing stem cells on a scaffold comprising a biosynthetic hydrogel of polymer and fibrinogen.

Another aspect of this application relates to a method for promoting tooth vitality in a subject in need thereof. The method comprises injecting a hydrogel-based scaffold comprising a polymeric hydrogel and fibrinogen into a tooth of the subject.

BRIEF DESCRIPTION OF THE FIGURES

FIG. 5A shows cell viability visualized using Live/Dead staining. FIG. 5B shows results of hematoxylin and eosin y staining. FIG. 5C is a bar graph comparing cell numbers normalized by gel wet weight on the scaffolds at days 1, 7, 21, 28 and 42.

FIG. 6A is a bar graph depicting collagen content at days 1, 7, 21, 28 and 42 as compared to wet weight of the scaffold. FIG. 6B is a bar graph depicting collagen content at days 1, 7, 21, 28 and 42 as compared to cell number. FIG. 6C shows results of the picrosirius staining.

FIG. 7A shows immunohistochemical staining on day 42 with cells producing both collagen type I and III in PEG-fibrinogen hydrogel scaffolds of this application with fibrinogen concentrations of 7.7, 8.5 and 9 mg/ml. Dentin sialophosphoprotein (FIG. 7B) and ALP gene expression (FIG. 7C) of cells cultured for 7 and 28 days in PEG-fibrinogen hydrogel scaffolds of this application with fibrinogen concentrations of 7.7, 8.5 and 9 mg/ml were also determined.

FIG. 8A is a bar graph showing ALP activity determined at days 1, 7, 21, 28 and 42 in hydrogel scaffolds of this application with fibrinogen concentrations of 7.7, 8.5 and 9 mg/ml. FIG. 8B shows results of alzarin red staining indicative of the presence of minerals including calcium in hydrogel scaffolds of this application with fibrinogen concentrations of 7.7, 8.5 and 9 mg/ml at days 1 and 42.

DETAILED DESCRIPTION

Definitions

Figure 1:
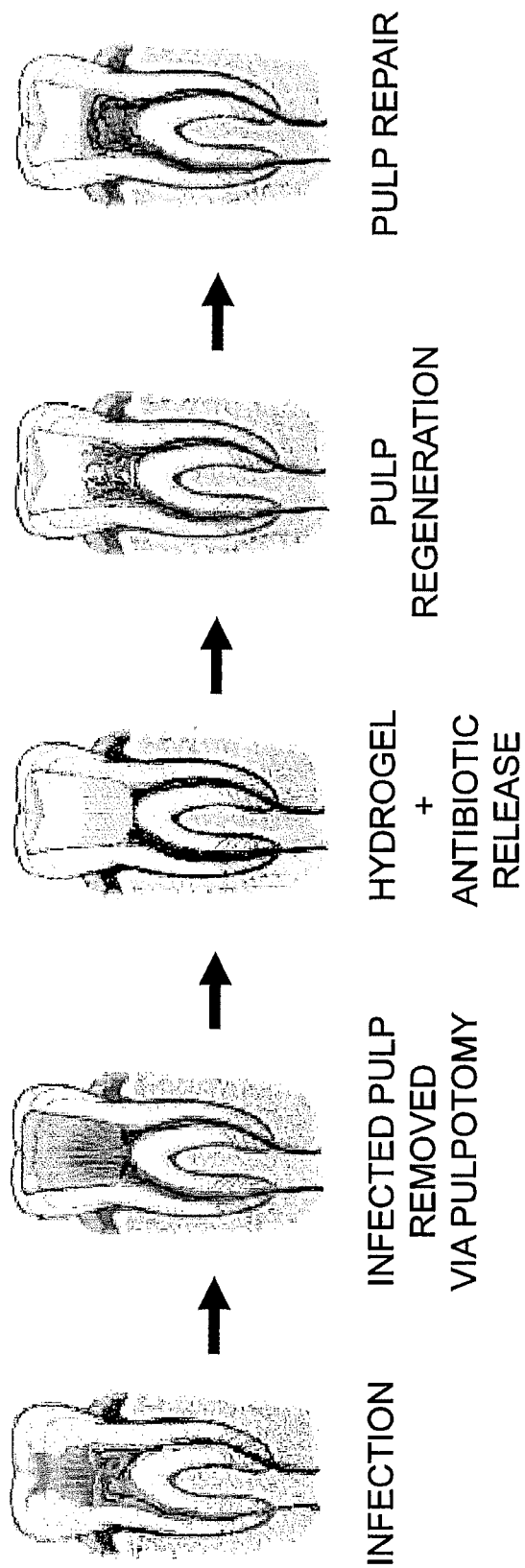
FIG. 1 is a diagram showing steps involved in use of a hydrogel-based scaffold of this application in endodontic therapy. In the nonlimiting embodiment depicted in FIG. 1, the hydrogel-based scaffold further contains an antibiotic.

In order to facilitate an understanding of the material which follows, one may refer to Freshney, R. Ian. *Culture of Animal Cells—A Manual of Basic Technique* (New York: Wiley-Liss, 2000) for certain frequently occurring methodologies and/or terms which are described therein.

Unless defined otherwise, all technical and scientific terms used herein have the meaning commonly understood by a person skilled in the art to which this invention belongs. However, except as otherwise expressly provided herein, each of the following terms, as used in this application, shall have the meaning set forth below.

As used herein, "ALP activity" shall mean alkaline phosphatase activity.

As used herein, a "biocompatible" material is a synthetic or natural material used to replace part of a living system or to function in intimate contact with living tissue. Biocompatible materials are intended to interface with biological systems to evaluate, treat, augment or replace any tissue, organ or function of the body. The biocompatible material has the ability to perform with an appropriate host response in a specific application and does not have toxic or injurious effects on biological systems. Nonlimiting examples of biocompatible materials include a biocompatible ceramic, a biocompatible polymer or a biocompatible hydrogel.

As used herein, "biodegradable" means that the material, once implanted into a host, will begin to degrade.

As used herein, "biomimetic" shall mean a resemblance of a synthesized material to a substance that occurs naturally in a human body and which is not substantially rejected by (e.g., does not cause an unacceptable adverse reaction in) the human body. When used in connection with the tissue scaffolds, biomimetic means that the scaffold is substantially biologically inert (i.e., will not cause an unacceptable immune response/rejection) and is designed to resemble a structure (e.g., soft tissue anatomy) that occurs naturally in a mammalian, e.g., human, body and that promotes healing when implanted into the body.

As used herein, "effective amount" and/or "sufficient concentration" shall mean a level, concentration, combination or ratio of one or more components added to the scaffold which promotes differentiation of stem cells to a selected cell type and/or enhances proliferation of desired cells.

As used herein, "hydrogel" shall mean any colloid in which the particles are in the external or dispersion phase and water is in the internal or dispersed phase.

As used herein, "polymer" means a chemical compound or mixture of compounds formed by polymerization and including repeating structural units. Polymers may be constructed in multiple forms and compositions or combinations of compositions.

As used herein, "stem cell" means any unspecialized cell that has the potential to develop into many different cell types in the body. Nonlimiting examples of "stem cells" include mesenchymal stem cells, embryonic stem cells and induced pluripotent cells. In one embodiment, for purposes of this application, the stem cells develop into human dental pulp cells.

As used herein, "synthetic" shall mean that the material is not of a human or animal origin.

As used herein, all numerical ranges provided are intended to expressly include at least the endpoints and all numbers that fall between the endpoints of ranges.

The following embodiments are provided to further illustrate the scaffolds and methods for production and use of the scaffolds of this application. These embodiments are illustrative only and are not intended to limit the scope of this application in any way.

Embodiments

Provided in this disclosure are scaffolds for dental pulp tissue engineering as well as methods for their production and use. FIG. 1 is a diagram showing steps involved in use of the hydrogel-based scaffold in endodontic therapy. As shown therein, upon identification of an infected tooth, the infected pulp is removed via pulpectomy. A hydrogel-based scaffold of this application is then inserted into the tooth resulting in pulp regeneration and repair.

Scaffolds of this application comprise a biosynthetic hydrogel of polymer and fibrinogen.

Preferred are polymers that can be functionalized by a protein or peptide fragment and allow cell spreading within the gel. A nonlimiting example of a polymer useful in the scaffold of the present invention is polyethylene glycol (PEG). Additional nonlimiting examples of polymers include agarose, carrageenan, polyethylene oxide, tetraethylene glycol, triethylene glycol, trimethylolpropane ethoxylate, pentaerythritol ethoxylate, hyaluronic acid, thiosulfonate polymer derivatives, polyvinylpyrrolidone-polyethylene glycol-agar, collagen, dextran, heparin, hydroxyalkyl cellulose, chondroitin sulfate, dermatan sulfate, heparan sulfate, keratan sulfate, dextran sulfate, pentosan polysulfate, chitosan, alginates, pectins, agars, glucomannans, galactomannans, maltodextrin, amylose, polyalditol, alginate, alginate-based gels cross-linked with calcium, gelatin, silk, proteoglycans, poly(glycolic) acid, polymeric chains of methoxypoly(ethylene glycol) monomethacrylate, chitin, poly(hydroxyalkyl methacrylate), poly(electrolyte complexes), poly(vinylacetate) cross-linked with hydrolysable bonds, water-swellable N-vinyl lactams, carbomer resins, starch graft copolymers, acrylate polymers, polyacrylamides, polyacrylic acid, ester crosslinked polyglucans, poly(lactic)acid, Puramatrix™, self-assembly peptide hydrogels, and derivatives and combinations thereof.

Scaffolds of this application further comprise fibrinogen and/or another agent such as, but not limited to collagen, albumin, or synthetic biomolecules or peptides. By fibrinogen, it is meant to include intact fibrinogen or a fibrinogen fragment. In one embodiment, fibrinogen is present in the scaffold at a concentration sufficient for promoting pulp cell growth and biosynthesis, regulating pulp cell infiltration into, migration and morphology, or both. As demonstrated herein, fibrinogen concentrations of at least 7 mg/ml, more preferably at least 8 mg/ml, more preferably at least 9 mg/ml can be used in the scaffolds to promote pulp cell growth and biosynthesis. Accordingly, it is expected that fibrinogen concentrations ranging from about 5 to 10 mg/ml can be used.

In one embodiment, the scaffold comprises a composite polymeric hydrogel referred to herein as PEG-F. In one embodiment of this composite, 0 to 40 mg/ml of PEG-diacrylate is added. Preferred is addition of about 10 to about 20 mg/ml, more preferably about 11 to about 16 mg/ml of PEG-diacrylate, to form PEG-fibrinogen monomers.

Further, additional PEG-diacrylate may be added to the scaffold to enhance hydrogel mechanical properties. In one embodiment, additional PEG-diacrylate is added prior to crosslinking. In this embodiment, the additional PEG-diacrylate content is from about 1.7% to about 3.2% w/v.

Figure 2:
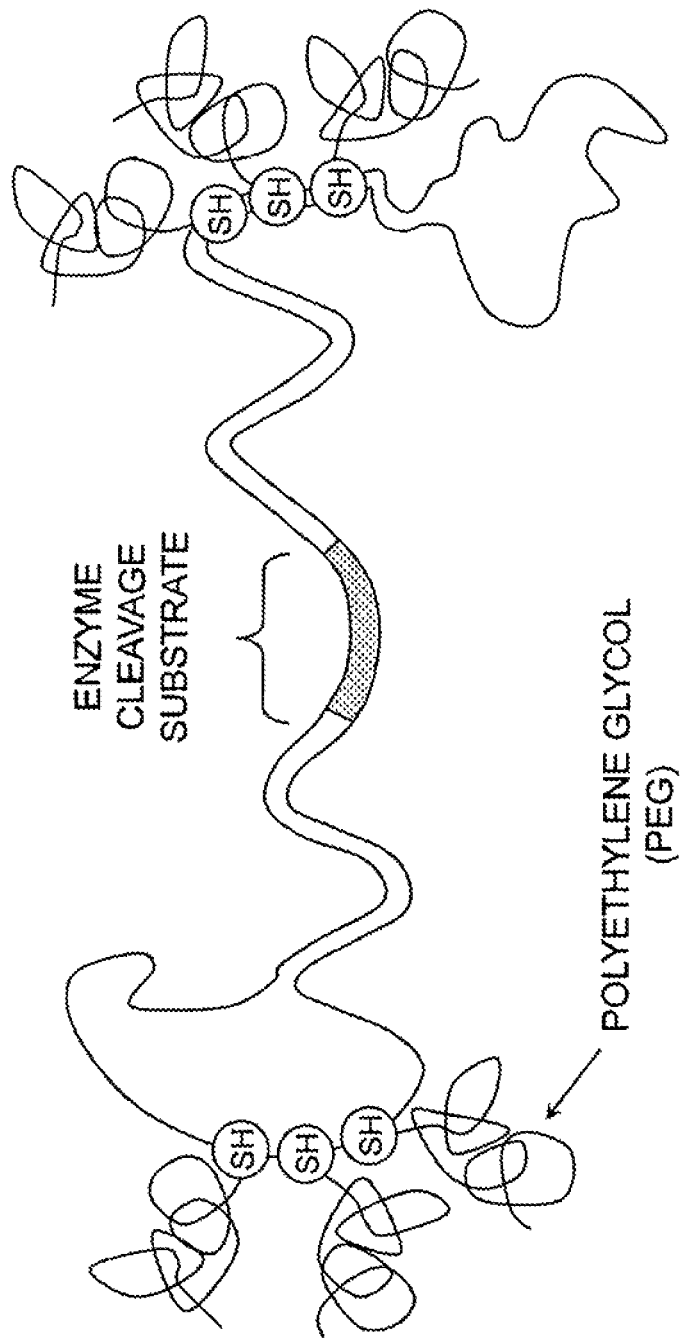
FIG. 2 provides the structure of PEG-F with a fibrinogen backbone crosslinked with polyethylene glycol-diacrylate.

The molecular structure of PEG-F showing the fibrinogen backbone crosslinked with polyethylene glycol-diacrylate is depicted in FIG. 2. A diagram of the steps involved in synthesis of the PEG-F is depicted in FIG. 2 and described in more detail in Example 1. The PEG-F hydrogel has biocompatibility and its physical characteristics can be controlled by varying polymer weight percent, molecular chain length, and crosslinking density. An additional advantage of PEG-F hydrogels is their ability to undergo a controlled liquid-to-solid transition (gelation) in the presence of a cell suspension. The PEG-F gelation reaction can be carried out under nontoxic conditions in the presence of a photoinitiator or by mixing a two-part reactive solution of functionalized PEG and crosslinking the constituents. The fibrinogen backbone of the PEG-fibrinogen gel serves as a natural substrate for tissue remodeling, and provides the PEG-fibrinogen hydrogels an inherent degradability by way of cell-activated protease activity and cell specific adhesivity that are not available with PEG alone.

As will be understood by the skilled artisan upon reading this disclosure, any of the parameters in the scaffold, including fibrinogen content, crosslinker content and/or PEGDA:fibrinogen ratio can be modified to direct cell response and dental pulp formation.

Nonlimiting examples of alternative composite polymeric hydrogels useful in these scaffolds include PEG-collagen, PEG-albumin, and PEG-synthetic peptide that contains RGD sites with proteolytic degradation sites.

In one embodiment the hydrogel-based scaffold of this application is injectable. In one embodiment, the hydrogel-based scaffold is injectable in situ. In a further embodiment, the hydrogel-based scaffold of this application solidifies in vivo. In yet another embodiment, the hydrogel-based scaffold solidifies in vivo with non-toxic components. In one nonlimiting embodiment, UV light at a wavelength 365 nm with photoinitiator is used.

Scaffolds of this application may further comprise an effective amount of antibiotic useful in preventing pulp infection. A nonlimiting example of such an antibiotic is ciprofloxacin.

Scaffolds of this application may further comprise an effective amount of an angiogenic factors. Non limiting examples include, but are not limited to, VEGF, PDGF, PRP and combinations thereof. PRP and/or fibroblastic growth factors may also be added to the scaffolds.

Acellular forms of the scaffold of this application drive host cell infiltration and/or migration resulting in new pulp from these host cells.

The hydrogel-based scaffold of this application may further comprise stem cells for tooth pulp repair and regeneration and/or dental pulp cells and/or endothelial cells. In one embodiment, two or more of these cell types are co-cultures together on the scaffold. Preferred is that the scaffold be seeded with at least 3.2 million cells per ml.

Experiments were performed examining gel characteristics as well as cell viability, cell proliferation, alkaline phosphatase or ALP activity, collagen content, and corresponding histology including collagen type I and III as well as expression of dentin sialophosphoprotein (DSPP) and ALP in PEG-F scaffolds with fibrinogen concentrations ranging from 7.7 to 9 mg/ml seeded with human dental pulp cells. Results from these experiments are shown in FIGS. 4A through 8B.

Figure 4A:
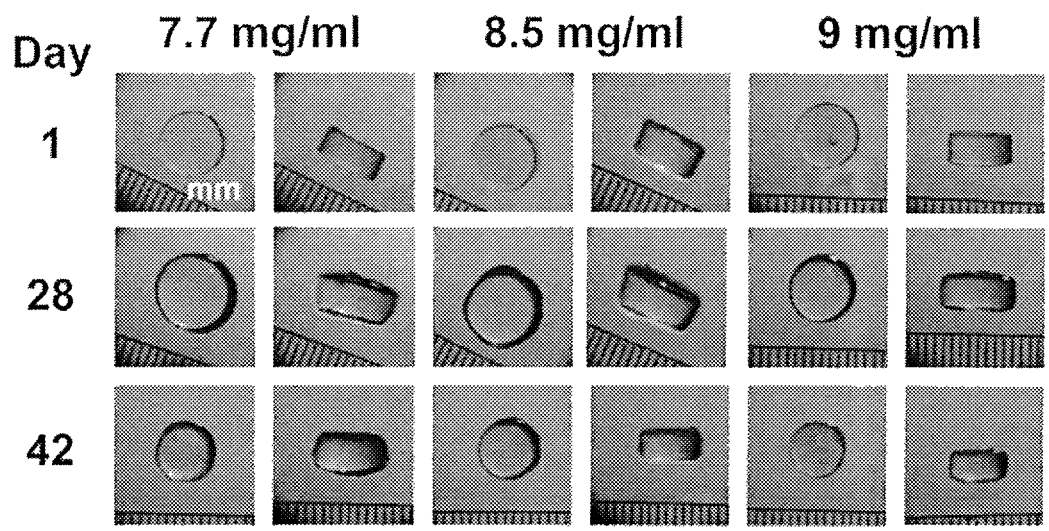
FIGS. 4A through 4D show characteristics of hydrogel scaffolds of this application with fibrinogen concentrations of 7.7, 8.5 and 9 mg/ml. Images of the gel diameters at days 1, 28 and 42 are shown in FIG. 4A. Characteristics examined included gel weight (FIG. 4B), gel diameter (FIG. 4C) and swelling ratio (FIG. 4D), each measured at day 1, 7, 21, 28 and 42.
Figure 4B:
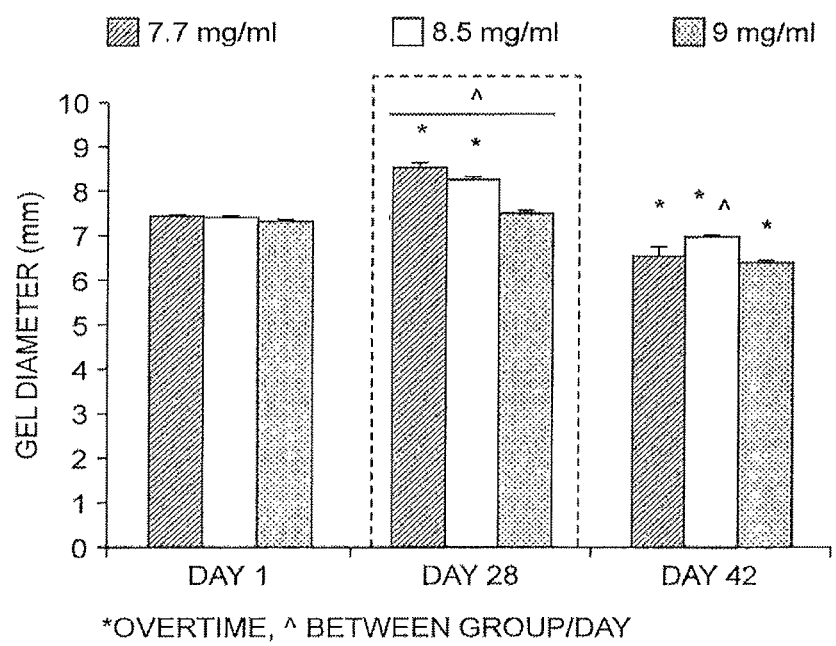
Figure 4C:
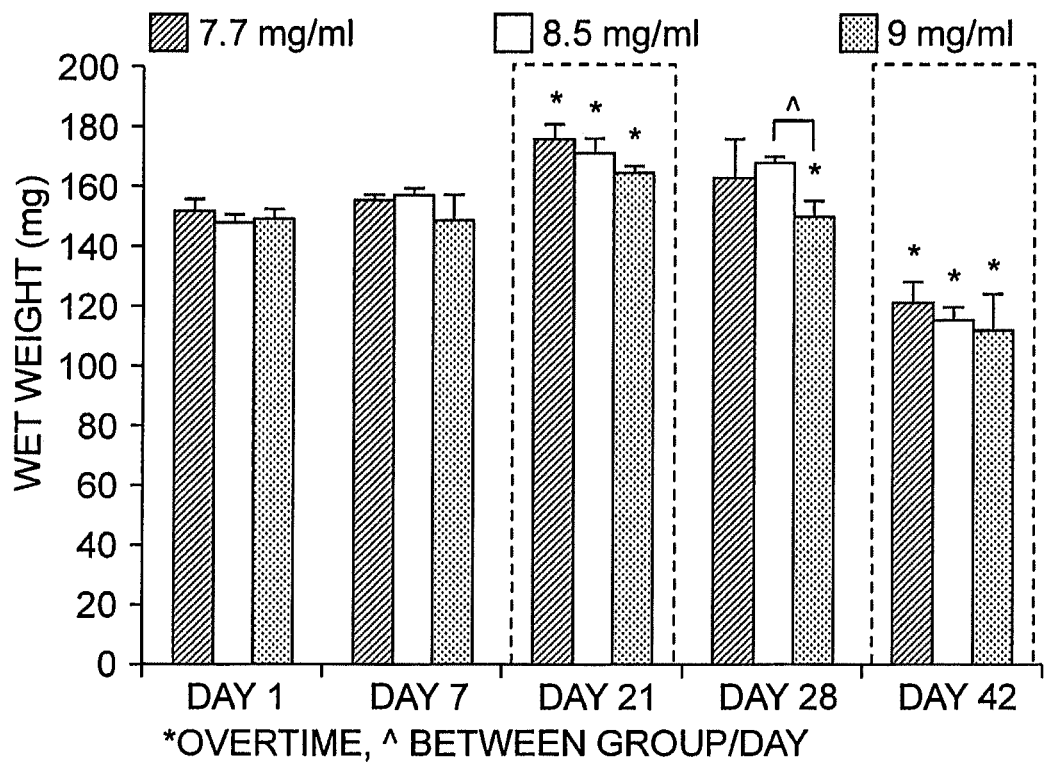
Figure 4D:
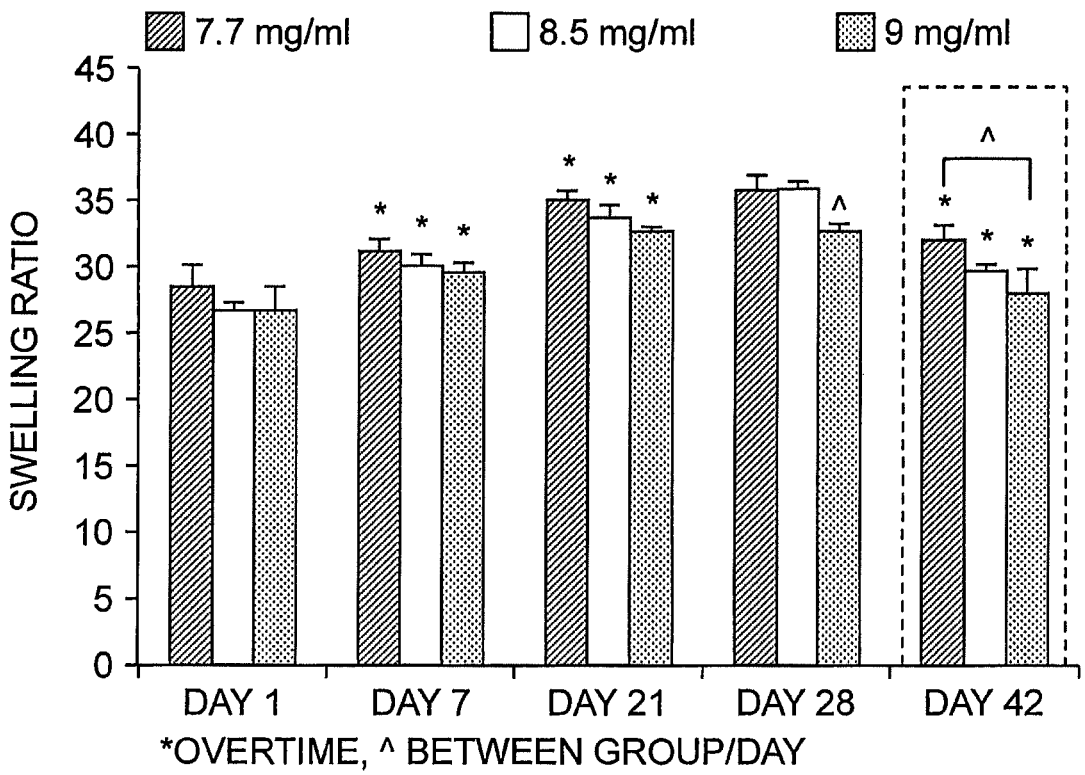

Characteristics of a hydrogel based scaffold of this application are depicted in FIGS. 4A through 4C. As shown therein, gel diameter changed overtime for all fibrinogen concentrations (see FIG. 4B). On day 28, a higher fibrinogen concentration of 9 mg/ml resulted in smaller diameter as shown from the images in FIG. 4A on day 42 and FIG. 4B. Gel wet weight, as shown in FIG. 4C, significantly increased on day 21 and decreased on day 42 for all groups from proteolytic degradation. In addition, gel swelling ratio in the highest fibrinogen concentration of 9 mg/ml was significantly lower than the lowest fibrinogen concentration of 7.7 mg/ml on day 42 (see FIG. 4D). In addition, the hydrogels after day 21 were mostly comprised of collagen produced from the pulp cells. From the collagen data, collagen per wet weight of the scaffold with the highest fibrinogen concentration was highest on day 42, resulting in lower swelling ratio and smaller diameter. Studies showed that fibroblasts contract collagen.

Figure 5A:
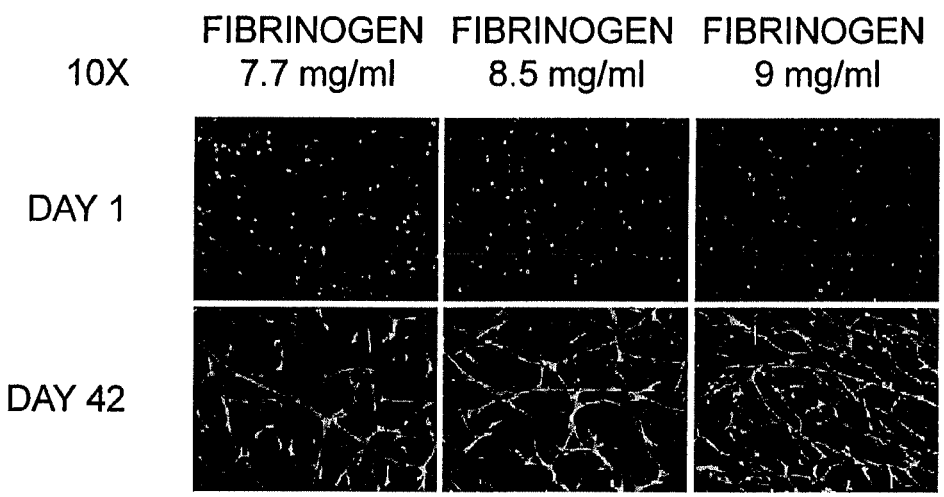
FIGS. 5A through 5C show results of experiments comparing cell viability and proliferation of chondrocytes seeded on hydrogel scaffolds of this application with fibrinogen concentrations of 7.7, 8.5 and 9 mg/ml.
Figure 5B:
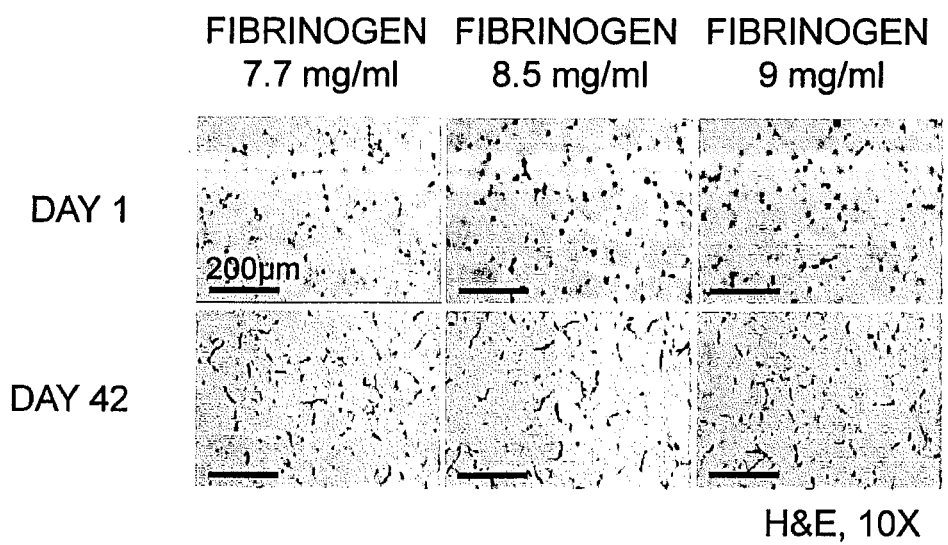
Figure 5C:
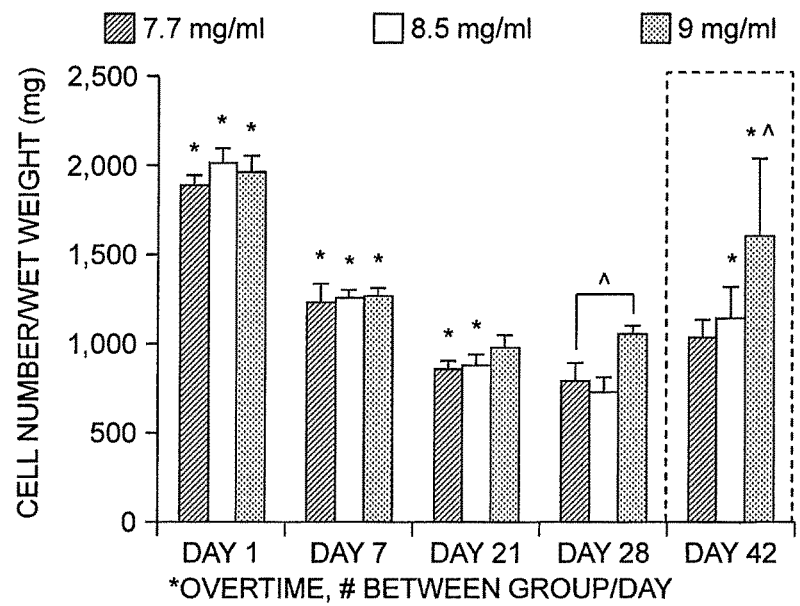

Results from cell viability and cell proliferation experiments are shown in FIGS. 5A through 5C. Live and dead staining as shown in FIGS. 5A and 5B, respectively, showed that cells remain viable overtime at all fibrinogen concentrations examined. Changes in cell morphology and spreading were found over time for all groups with cells exhibiting a physiologically relevant spindle-shape over time. The cell network was densest in the group with the highest fibrinogen concentration of 9 mg/ml on day 42 as shown by live and dead staining in FIG. 5A and cell number data on day 42. As shown in FIG. 5C, cell number in all PEG-fibrinogen groups decreased significantly on day 7 and stabilized overtime. By day 42, cell number in the 9 mg/ml group was the highest and it increased significantly over time.

Figure 6A:
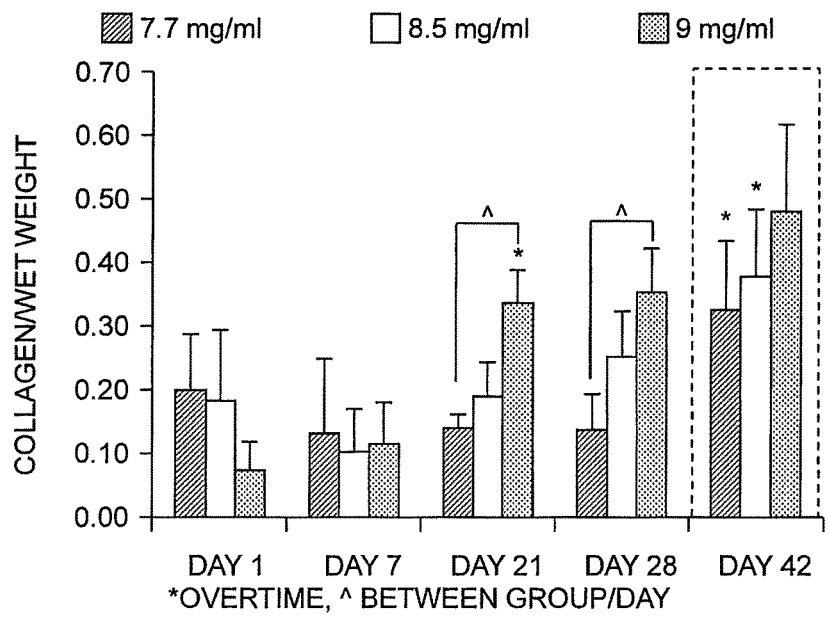
FIGS. 6A through 6C show results of experiments measuring matrix deposition and more specifically collagen content as confirmed by picrosirius staining of chondrocytes seeded on hydrogel scaffolds of this application with fibrinogen concentrations of 7.7, 8.5 and 9 mg/ml.
Figure 6B:
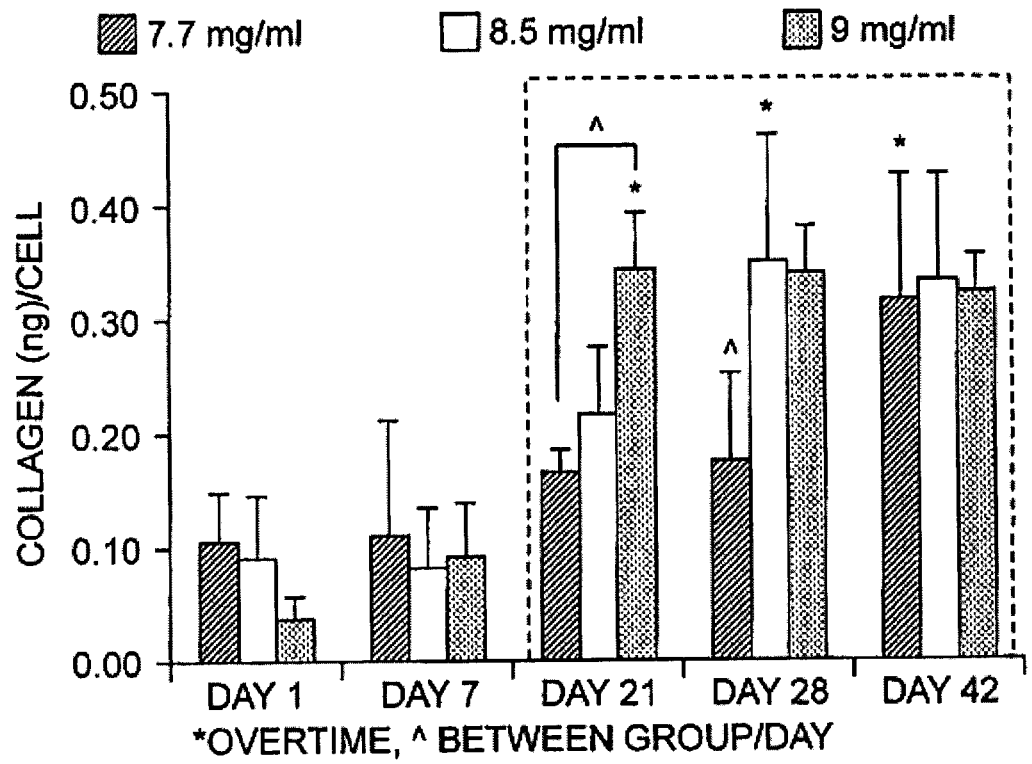
Figure 6C:
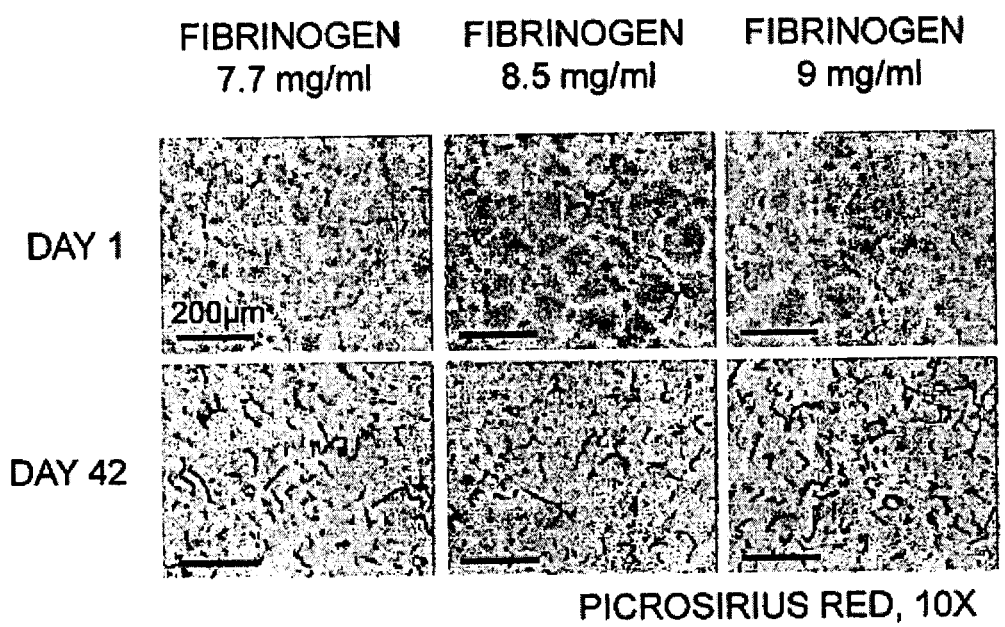

Matrix deposition inclusive of collagen content for hydrogel-based scaffolds of this application is depicted in FIGS. 6A through 6C. A significant increase in collagen content was found for all groups over time as confirmed by picrosirius red staining (see FIGS. 6A and 6B, respectively). From collagen per cell results depicted in FIG. 6C, however, it was found that earlier and higher collagen production occurred in the higher fibrinogen groups.

Figure 7A:
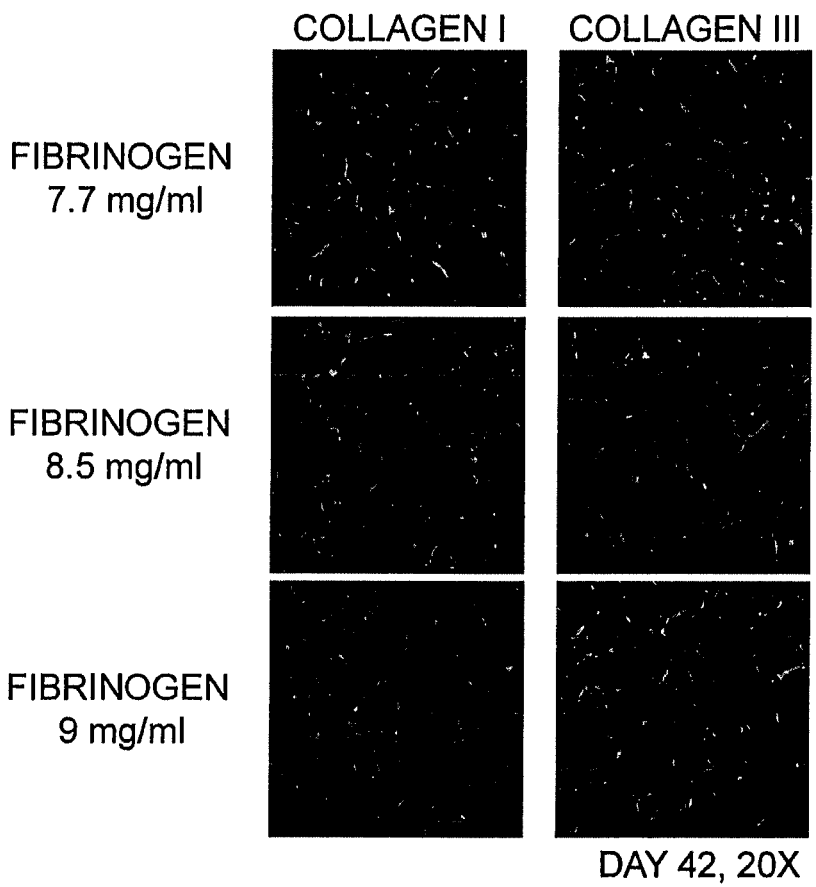
FIGS. 7A through 7C show results from experiments measuring matrix composition.
Figure 7B:
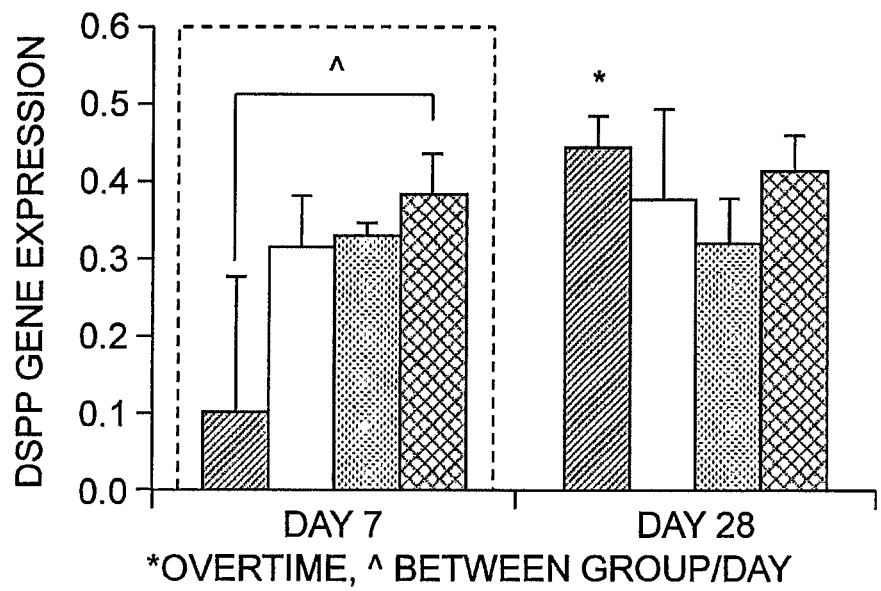
Figure 7C:
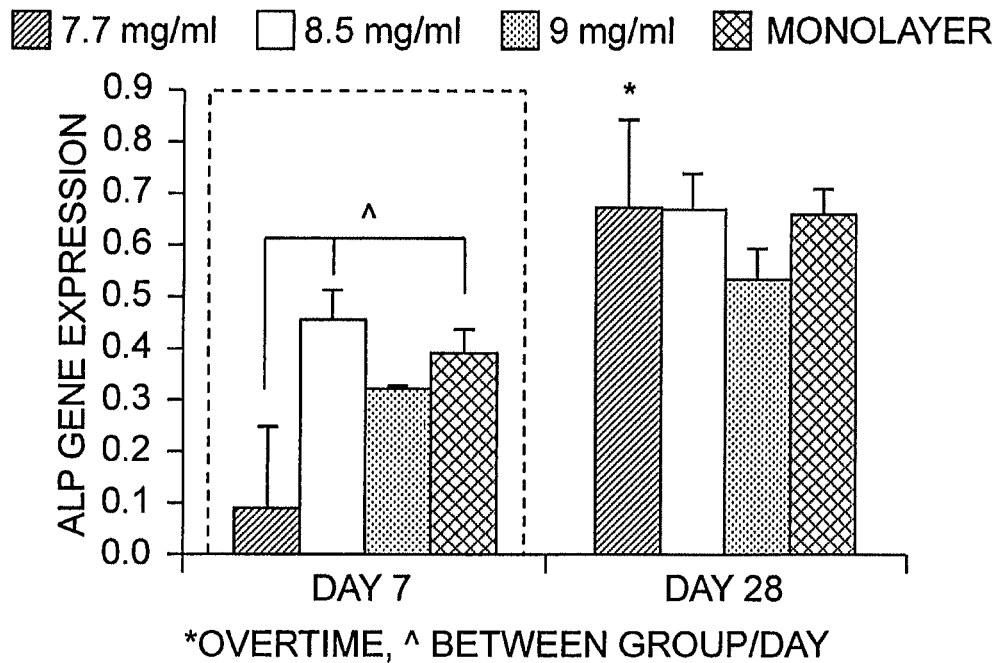

Matrix composition was also examined and results are shown in FIGS. 7A through 7C. Immunohistochemical staining on day 42 showed that cells produced both collagen type I and III in all the PEG-fibrinogen hydrogels (See FIG. 7A). Thus, the hydrogel-based scaffolds of this application are expected to modulate biosynthesis of a variety of cell types. Further, as shown in FIGS. 7B and 7C, respectively, dentin sialophosphoprotein and ALP gene expression of cells cultured in PEG-Fibrinogen was downregulated at the lowest fibrinogen concentration of 7.7 mg/ml as compared to monolayer on day 7. However, levels of dentin sialophosphoprotein and ALP gene expression of cells cultured in all PEG-fibrinogen groups were similar to monolayer by day 28. Dentin sialophosphoprotein is an odontoblast-related gene, high expression of which corresponds to mineralization and dentin formation.

Figure 8A:
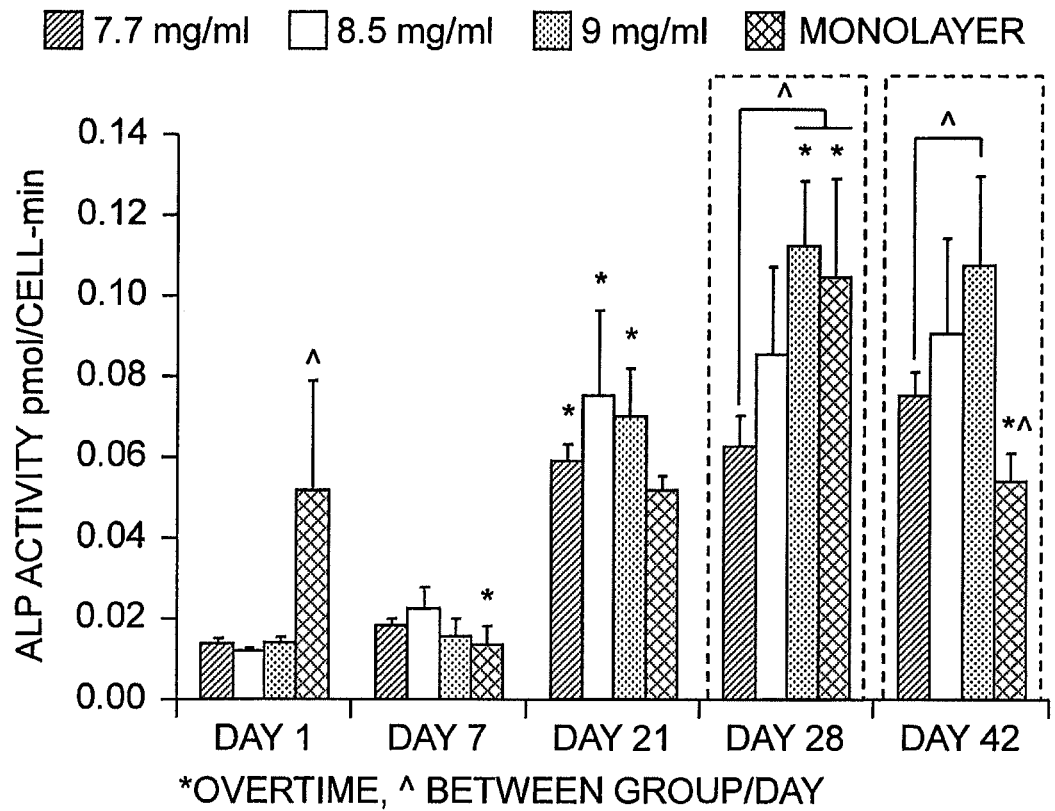
FIGS. 8A and 8B show the mineralization potential of hydrogel scaffolds of this application. ALP activity increased overtime for cells cultured in PEG-Fibrinogen hydrogels.
Figure 8B:
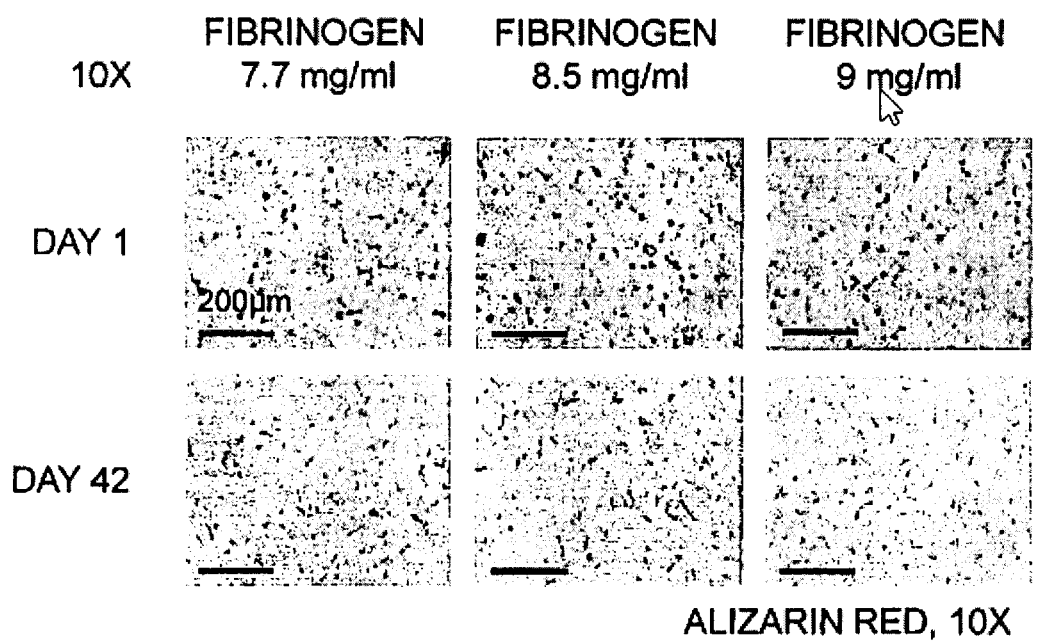

ALP mineralization potential was also examined and results are shown in FIGS. 8A and 8B. As shown in FIG. 8A, ALP activity increased overtime for cells cultured in all PEG-fibrinogen hydrogels. The highest ALP activity was detected in the 9 mg/ml group on both day 28 and 42. However, alzarin red staining as shown in FIG. 8B showed no calcium staining overtime in any of the groups.

Accordingly, the disclosed subject matter of this application also relates to use of the hydrogel-based scaffolds of this application in promoting pulp cell growth and biosynthesis. In one embodiment, pulp cell growth and biosynthesis is promoted by modulating fibrinogen concentration in the hydrogel-based scaffold. In one embodiment, pulp cell growth and biosynthesis is promoted by increasing fibrinogen concentration in the hydrogel-based scaffold. In one embodiment, pulp cell growth and biosynthesis is promoted by increasing fibrinogen concentration in the hydrogel-based scaffold to at least 5-10 mg/ml, more preferably at least 8 mg/ml, more preferably at least 9 mg/ml.

The disclosed subject matter of this application also relates to use of the hydrogel based scaffolds in regulating cell infiltration into, migration and morphology within a hydrogel-based scaffold. In one embodiment, pulp cell infiltration into, migration and morphology is regulated by modulating fibrinogen concentration in the hydrogel-based scaffold. In one embodiment, pulp cell infiltration into, migration and morphology is regulated by increasing fibrinogen concentration in the hydrogel-based scaffold. In one embodiment, pulp cell growth and biosynthesis is promoted by increasing fibrinogen concentration in the hydrogel-based scaffold to at least 5-10 mg/ml, more preferably at least 8 mg/ml, more preferably at least 9 mg/ml. Alternatively, or in addition, crosslinker content and/or PEG-diacrylate:fibrinogen ratio in the hydrogel-based scaffold can be modified. In one embodiment, the cross linker content ranges from about 0.05% to about 0.2% w/v. In one embodiment, PEG-diacrylate content is from about 1.7% to about 3.2% w/v.

In addition, the disclosed subject matter of this application relates to in vitro methods for differentiation and expansion of stem cells into patient-specific dental pulp cells. In one embodiment, stem cells are cultured on hydrogel-based scaffolds with increased fibrinogen concentrations. In one embodiment, differentiation and expansion of stem cells is promoted by increasing fibrinogen concentration in the hydrogel-based scaffold to at least 5-10 mg/ml, more preferably at least 8 mg/ml, more preferably at least 9 mg/ml. Alternatively, or in addition, crosslinker content and/or PEG-diacrylate:fibrinogen ratio in the hydrogel-based scaffold can be modified. In one embodiment, the cross linker content ranges from about 0.05% to about 0.2% w/v. In one embodiment, PEG-diacrylate content is from about 1.7% to about 3.2% w/v.

The disclosed subject matter of this application also relates to methods for promoting tooth vitality in a subject in need thereof by injecting, implanting and/or molding a hydrogel-based scaffold of this application into the tooth of the subject. These hydrogel-based scaffolds will protect against infection, promote self-repair and preserve tooth vitality in the subject.

The following section provides further illustration of the methods and apparatuses of the present invention. These examples are illustrative only and are not intended to limit the scope of the invention in any way. The following disclosure should not be construed as limiting the invention in any way. One of skill in the art will appreciate that numerous modifications, combinations, rearrangements, etc. are possible without exceeding the scope of the invention. While this invention has been described with an emphasis upon various embodiments, it will be understood by those of ordinary skill in the art that variations of the disclosed embodiments can be used, and that it is intended that the invention can be practiced otherwise than as specifically described herein.

EXAMPLES

Example 1

PEG-Fibrinogen (PEG-F) Synthesis

PEG-F synthesis was facilitated by conjugating hydrophilic polyethylene glycol (PEG) to reconstituted fibrinogen, retaining much of the functionality of fibrinogen while maintaining/improving the physical properties of PEG. The PEG gelation reaction can be carried out under non-toxic conditions either with photoinitiators or by mixing a two-part reactive solution of functionalized PEG and crosslinking the constituents. In these experiments, for PEG-diacrylate (PEG-DA) synthesis, the acrylation of PEG-OH (Fluka, Mw=10 kDa) was carried out under argon by reacting a dichloromethane solution of PEG-PH (Aldrich) with acryloyl chloride (Sigma) and triethylamine (Fluka) at a molar ratio of 1:5:1 relative to —OH groups. The final product was precipitated in ice-cold diethyl ether and dried under vacuum for 48 hours. Proton NMR ($^1$HNMR) was used to validate end-group conversion and to verify purity of the final product.

Figure 3:
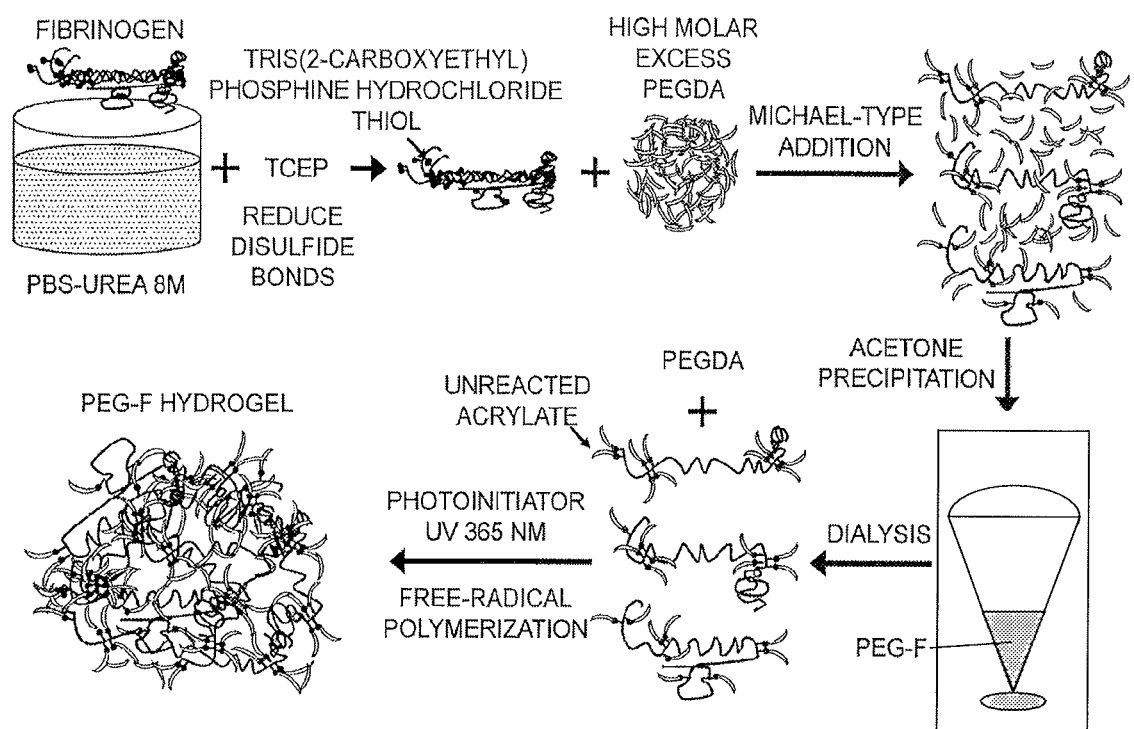
FIG. 3 is a diagram of the steps involved in synthesis of the PEG-F depicted in FIG. 2. In the first step, purified fibrinogen is dissolved in phosphate buffered saline containing high urea concentration to improve protein solubility and to eliminate steric hindrance by straightening its chain. In the second step, the disulfide bonds in the fibrinogen are reduced using a Tris(2-carboxyethyl) phosphine hydrochloride. The fibrinogen is dissociated into the alpha, beta, and gamma fragments of the molecule, leaving reactive thiols exposed. In the third step, the high molar excess of PEG-diacrylate (PEGDA) self-selectively reacts with free thiols on the fibrinogen molecule by Michael-type addition reaction. In the fourth step, PEG-fibrinogen molecules are purified from the excess PEGDA and urea by acetone precipitation and dialysis. In the fifth step, a solution of PEG-fibrinogen whose structural properties could be adjusted with addition of PEGDA is exposed to UV light and photoinitiator to initiate a free-radical polymerization between the unreacted acrylates on the PEGDA resulting in a solid hydrogel network.

Next, as shown in FIG. 3, PEGylation of fibrinogen was achieved by adding tris(2-carboxyethylphosphine hydrochloride (TCEP, Sigma) to bovine fibrinogen (7 mg/ml, Sigma) in 100 mM PBS with 8M urea (molar ratio of 4:1 TCEP to fibrinogen cysteines). Linear PEG-DA (10-kDa) was attached to cysteine residues of fibrinogen via Michael-type addition, where PEG-DA reacts for 3 hours with protein at a 4:1 molar ratio of PEG to fibrinogen cysteines. The PEGylated protein product was then purified from excess PEG-DA and urea by acetone precipitation and dialysis. For dialysis, the PEGylated protein was re-dissolved in PBS with 8M urea at 15 mg/ml final fibrinogen concentration and then dialyzed against PBS at 4° C. for two days (Spectrum, 6-8 kDa MW cut-off). The final product was characterized in accordance with established methods with net fibrinogen concentration determined by BCA protein assay.

For hydrogel formation, the PEGylated fibrinogen was crosslinked via a free-radical polymerization between unreacted acrylates on PEG-DA. Briefly, PEGylated fibrinogen precursor was combined with a 0.1% (w/v) photoinitiator solution prepared by dissolving 10% w/v IIRGACURE2959 (CIBA) in 70% ethanol. The mixture was photopolymerized in a custom mold for 5 minutes with UV light (365 nm, 15 mW/cm$^2$).

Example 2

Hydrogel Wet Weight, Dry Weight and Swelling Ratio

Samples of hydrogel scaffolds of this application with fibrinogen concentrations of 7.7, 8.5 and 9 mg/ml were washed in PBS, weighed for sample wet weight and desiccated for 24 hours (CentriVap Concentrator, Labconco Co., Kansas City, Mo.), after which scaffolds were weighed for dry weight and swelling ratio (n=6) was calculated as wet weight per dry weight.

Example 3

Seeding of Cells on Scaffolds

Human dental pulp cells from explant culture were seeded with 4.8 million cells per milliliter in PEG-fibrinogen at three fibrinogen concentrations: 7.7, 8.5 and 9 mg/ml, photopolymerized with 0.1% photoinitiator, and maintained in fully supplemented medium with ascorbic acid. Monolayer was used as a control. Samples were analyzed at 1, 7, 21, 28, and 42 days for cell viability, cell proliferation, alkaline phosphatase or ALP activity, collagen content, and corresponding histology including collagen type I and III. The expression of dentin sialophosphoprotein (DSPP) and ALP were determined using RT-PCR.

Example 4

Cell Viability

Cell viability (n=2) was visualized using Live/Dead staining (Molecular Probes, Eugene, Oreg.), following the manufacturer's suggested protocols. After washing in PBS, samples were imaged under confocal microscope (Olympus Fluoview FV1000, Center Valley, Pa.) at 473 nm excitation/519 nm emission wavelengths for FITC and 559 nm excitation/612 nm emission for Texas Red.

Example 5

Cell Proliferation

Cell proliferation (n=6) was determined using the PICOGREEN total DNA assay (molecular Probes, Eugene, Oreg.). Briefly, the samples were first rinsed with PBS and 500 μl of 0.1% Triton-X solution (Sigma-Aldrich, St. Louis, Mo.) was used to lyse the cells. An aliquot of the sample (25 μl) was then added to 175 μl of the PICOGREEN working solution. Fluorescence was measured with a microplate reader (Tecan, Research Triangle Park, N.C.), at the excitation and emission wavelengths of 485 and 535 nm, respectively. Total cell number was obtained by converting the amount of DNA per sample to cell number using the conversion factor of 8 pg DNA/cell.

Example 6

Measurement of Alkaline Phosphatase or ALP Activity

Mineralization potential was determined by measuring ALP activity using a colorimetric assay based on the hydrolysis of p-nitrophenyl phosphate (pNP-PO$_4$) to p-nitrophenol (pNP). Briefly, the samples were lysed in 0.1% Triton-X solution, then added to pNP-PO$_4$ solution (Sigma-Aldrich, St. Louis, Mo.) and allowed to react for 30 minutes at 37° C. The reaction was terminated with 0.1 N NaOH (Sigma-Aldrich, St. Louis, Mo.), and sample absorbance was measured at 415 nm using a microplate reader (Tecan, Research Triangle Park, N.C.).

Example 7

Collagen Content

Collagen deposition was quantified using a hydroxyproline assay based on alkaline hydrolysis of the tissue homogenate and subsequent determination of the free hydroxyproline in hydrolyzates. Briefly, the samples were first desiccated for 24 hours and then digested for 16 hours at 65° C. with papain (600 mg protein/ml, Sigma-Aldrich, St. Louis, Mo.) in 0.1M sodium acetate (Sigma-Aldrich, St. Louis, Mo.), 10 mM cysteine HCl (Sigma-Aldrich, St. Louis, Mo.), and 50 mM ethylenediaminetetraacetate (Sigma-Aldrich, St. Louis, Mo.). Samples were then hydrolyzed with 2N sodium hydroxide for 25 minutes and chloramine-T (Sigma) was added into hydrolyzed sample to oxidize the free hydroxyproline for the production of a pyrrole at room temperature for 25 minutes. Then, Ehrlich's reagent (Sigma-Aldrich, St. Louis, Mo.) was added to the products and incubated at 65° C. for 20 minutes resulting in the formation of a chromophore. The solution was transferred to 96-well plate and sample absorbance was measured at 555 nm using a microplate reader (Tecan, Research Triangle Park, N.C.).

Example 8

Histological Analysis

Hydrogels were fixed in 4% paraformaldehyde, stored in 70% ethanol, and embedded in paraffin and sectioned for 7 μm thickness. Sections were stained with hematoxylin and counterstained with eosin. Picrosirius red staining was used to stain collagen. Immunohistochemistry staining of collagen I and collagen III was done using type specific collagen antibody (Abcam) with FITC-conjugated secondary antibody solution and DAPI staining for cell nucleus. Alizarin Red S staining was used to stain calcium, indicative of mineralization. Sections were imaged under light microscope except for immunohistochemistry staining which used a confocal microscope at the excitation and emission wavelengths of 485 and 535 nm, respectively for collagen I and collagen III.

Example 9

Gene Expression Analysis

The expression of human dental pulp cell-related markers were determined using reverse transcription followed by polymerase chain reaction (RT-PCR). Total RNA of dental pulp cells was isolated using the TRIZOL (Invitrogen, Carlsbad, Calif.) extraction method, with the isolated RNA reverse-transcribed into cDNA using the SuperScript III First-Strand Synthesis System (Invitrogen). The cDNA product was then amplified for 40 cycles with recombinant Platinum Taq DNA polymerase (Invitrogen). PCR products were size-fractionated on a 1% w/v agarose gel and visualized by ethidium-bromide staining. Expression band intensities of relevant genes were analyzed semi-quantitatively by ImageJ and normalized to the housekeeping gene human glyceraldehyde-3-phosphate dehydrogenase (GAPDH).

Example 10

Statistical Analyses

Statistical Analyses were done using ANOVA and the Turkey-kramer post-hoc test for all pair-wise comparisons.

What is claimed is:

1. A hydrogel-based scaffold for dental pulp formation, said scaffold comprising
   a biosynthetic hydrogel of polymer, fibrinogen, and 1.0-2.0% v/v of PEG-diacrylate,
   wherein fibrinogen is present in the hydrogel-based scaffold at a concentration of 0.5-1.0% w/v for promoting pulp cell growth and biosynthesis, regulating pulp cell migration and morphology, or both.

2. The hydrogel-based scaffold of claim 1 wherein the polymer comprises polyethylene glycol.

3. The hydrogel-based scaffold of claim 1 which comprises an intact fibrinogen or a fibrinogen fragment.

4. The hydrogel-based scaffold of claim 1 further comprising additional PEG-diacrylate from 1.7% to 3.2% w/v.

5. The hydrogel-based scaffold of claim 1 which is injectable.

6. The hydrogel-based scaffold of claim 1 which solidifies in vivo.

7. The hydrogel-based scaffold of claim 1 which solidifies in vivo with non-toxic components.

8. The hydrogel-based scaffold of claim 1 wherein the fibrinogen concentration is at least 0.8% w/v.

9. The hydrogel-based scaffold of claim 1 further comprising an antibiotic.

10. The hydrogel-based scaffold of claim 1 further comprising stem cells for tooth pulp repair and regeneration and/or dental pulp cells and/or endothelial cells.

* * * * *